(12) United States Patent
Graziani et al.

(10) Patent No.: US 7,470,682 B2
(45) Date of Patent: Dec. 30, 2008

(54) RAPAMYCIN ANALOGUES AND THE USES THEREOF IN THE TREATMENT OF NEUROLOGICAL DISORDERS

(75) Inventors: Edmund Idris Graziani, Chestnut Ridge, NY (US); Kevin Pong, Robbinsville, NJ (US); Jerauld Skotnicki, Westfield, NJ (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/893,090

(22) Filed: Aug. 14, 2007

(65) Prior Publication Data

US 2008/0004264 A1 Jan. 3, 2008

Related U.S. Application Data

(63) Continuation of application No. 11/300,839, filed on Dec. 15, 2005, now Pat. No. 7,276,498.

(60) Provisional application No. 60/637,666, filed on Dec. 20, 2004.

(51) Int. Cl.
*A61K 31/395* (2006.01)
(52) U.S. Cl. .................. 514/229.5; 514/291
(58) Field of Classification Search .............. 514/229.5, 514/291
See application file for complete search history.

(56) References Cited

U.S. PATENT DOCUMENTS

| | | | |
|---|---|---|---|
| 3,491,092 | A | 1/1970 | Grignat et al. |
| 3,686,238 | A | 8/1972 | Zaffaroni et al. |
| 3,738,980 | A | 6/1973 | Bickel et al. |
| 3,900,465 | A | 8/1975 | Cricchio et al. |
| 3,905,981 | A | 9/1975 | Olofson et al. |
| 4,127,720 | A | 11/1978 | Juby et al. |
| 5,023,262 | A | 6/1991 | Caufield et al. |
| 5,525,610 | A | 6/1996 | Caufield et al. |
| 5,604,294 | A | 2/1997 | Luly et al. |
| 5,696,135 | A | 12/1997 | Steiner et al. |
| 5,717,092 | A | 2/1998 | Armistead et al. |
| 5,780,484 | A | 7/1998 | Zelle et al. |
| 5,798,355 | A | 8/1998 | Steiner et al. |
| 6,015,809 | A | 1/2000 | Zhu et al. |
| 6,187,784 | B1 | 2/2001 | Steiner et al. |
| 6,500,843 | B2 | 12/2002 | Steiner et al. |
| 6,624,302 | B2 | 9/2003 | Chu et al. |
| 7,273,874 | B2 | 9/2007 | Graziani et al. |
| 7,276,498 | B2 | 10/2007 | Graziani et al. |
| 2001/0036947 | A1 | 11/2001 | Steiner et al. |
| 2002/0151088 | A1 | 10/2002 | Molnar-Kimber et al. |
| 2004/0224394 | A1 | 11/2004 | Katz et al. |
| 2007/0142423 | A1 | 6/2007 | Graziani et al. |
| 2007/0213525 | A1 | 9/2007 | Graziani et al. |

FOREIGN PATENT DOCUMENTS

| | | |
|---|---|---|
| AU | 9516257 | 10/1995 |
| DE | 1445742 | 12/1968 |
| DE | 1545824 | 12/1969 |
| DE | 4021404 A1 | 1/1992 |
| EP | 0343560 A2 | 11/1989 |
| EP | 0 475 577 A1 | 8/1991 |
| EP | 0778023 A1 | 6/1997 |
| GB | 2249027 A | 4/1992 |
| JP | 08333256 | 12/1996 |
| WO | WO-91/19495 | 12/1991 |
| WO | WO-92/13862 | 8/1992 |
| WO | WO-93/04679 | 3/1993 |
| WO | WO-93/04680 | 3/1993 |
| WO | WO-94/02136 | 2/1994 |
| WO | WO-94/02485 | 2/1994 |
| WO | WO-94/25022 | 11/1994 |
| WO | WO-96/40140 | 12/1996 |

(Continued)

OTHER PUBLICATIONS

Cantley et al., "New Insights into Tumor Suppression: PTEC Suppresses Tumor Formation by Restraining the Phosphoinositide 3-Kinase/AKT Pathway" Proc. Natl. Acad. Sci. USA, 96:4240-4245 (Apr. 1999).

(Continued)

*Primary Examiner*—Bruck Kifle

(57) ABSTRACT

Compounds of the following structure, wherein $R_1$, $R_2$, $R_4$, $R_{4'}$, $R_6$, $R_7$, and $R_{15}$ are defined above, are provided:

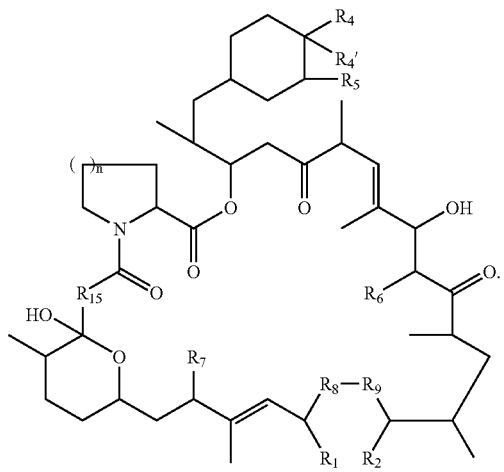

These compounds are useful in treating neurological disorders or complications due to stroke or head injury. The compounds are therefore useful as neuroprotective and neuroregenerative agents.

20 Claims, 6 Drawing Sheets

FOREIGN PATENT DOCUMENTS

| WO | WO-99/62483 | 12/1999 |
| --- | --- | --- |
| WO | WO-00/09109 | 2/2000 |
| WO | WO-00/09510 | 2/2000 |
| WO | WO-00/34239 | 6/2000 |
| WO | WO-01/18006 A1 | 3/2001 |
| WO | WO-01/34816 A1 | 5/2001 |
| WO | WO-01/87884 A2 | 11/2001 |
| WO | WO-03/018573 A1 | 3/2003 |
| WO | WO-03/018574 A1 | 3/2003 |
| WO | WO-2004/007709 A2 | 1/2004 |

OTHER PUBLICATIONS

Ali et al., "Mutational Spectra of PTEN/MMAC1 Gene: A Tumor Suppressor with Lipid Phosphatase Activity" J. Natl. Cancer. Inst., 91(22):1922 (Nov. 17, 1999).

Nave et al., "Mammalian Target of Rapamycin is a Direct Target for Protein Kinase B: Identification of a Convergence Point for Opposing Effects of Insulin and Amino-Acid Deficiency on Protein Translation" Biochem. J. 344:427-431 (Dec. 1, 1999).

Scott et al., "Evidence of Insulin-Stimulated Phosphorylation and Activation of the Mammalian Target of Rapamycin Mediated by a Protein Kinase B Signaling Pathway" Proc. Nat. Acad. Sci. USA, 95:7772-7777 (Jun. 1998).

Steiner et al., Neurotrophic Actions on Nonimmunosuppressive Analogues of Immunosuppressive Drugs FK506, Rapamycin and Cyclosporin Nat. Med., 3(4):421 (Apr. 1997).

Gold et al., "Neuroimmunophilin Ligands: The Development of Novel Neuroregenerative/Neuroprotective Compounds", Curr. Topics Med. Chem., 3:1368 (2003).

Birge et al., "A Role for Schwann Cells in the Neuroregenerative Effects of a Non-Immunosuppressive FK506 Derivative, JNJ460", Neuroscience, 124:351-366 (2004).

Tanaka et al., "Possibility of Non-Immunosuppressive Immunophilin Ligands as Potential Therapeutic Agents for Parkinson's Disease" Curr. Pharm. Design, 10:669-677 (2004).

Pong et al., "Therapeutic Implications for Immunophilin Ligands in the Treatment of Neurodegenerative Diseases" Curr. Drug Targets—CNS & Neurolog. Disorders, 2(6):349 (Dec. 2003).

Ocain et al., "A Nonimmunosuppressive Triene-Modified Rapamycin Analog is a Potent Inhibitor of Peptidyl Prolyl Cis-Trans Isomerase", Biochem. Biophys. Rse. Commun. 192(3):1340 (May 14, 1993).

Dickman et al., "Antifungal Rapamycin Analogues with Reduced Immunosuppressive Activity", Bioorg. & Med. Chem. Lett. 10(13):1405-1408 (Jul. 3, 2000).

Li et al., "Analysis of the Energetics of Gas-Phase Immunophilin-Ligand Complexes by Ion Spray Mass Spectrometry", J. Am. Chem. Soc., 116(17):7487 (1994).

Grigat et al., "2-Sulphonamido- and 2-Sulphonylhydrazido-benzoxazinones", English language Abstract of DE 1,545,824.

Nussbaumer et al., "New Tricyclic Heteroatom Containing Compounds for Arthritis", English language Abstract of DE 4,021,404.

Snyder et al, Immunophilins and the Nervous System, Nature Medicine, vol. 1, No. 1, pp. 32-37, (Jan. 1995).

Holt et al, Structure-Activity Studies of Synthetic FKBP Ligands as Peptidyl-Prolyl Isomerase Inhibitors, Biorganic & Medicinal Chemistry Letters, vol. 4, No. 2, pp. 315-320, (1994).

RAPAMYCIN ANALOGUES AND THE USES THEREOF IN THE TREATMENT OF NEUROLOGICAL DISORDERS

CROSS-REFERENCE TO RELATED APPLICATIONS

This application is a continuation of U.S. patent application Ser. No. 11/300,839, filed Dec. 15, 2005, which claims the benefit under 35 USC 119(e) of prior U.S. Provisional Patent Application No. 60/637,666, filed Dec. 20, 2004.

BACKGROUND OF THE INVENTION

The present invention provides rapamycin analogues and their use in the treatment of neurological, proliferative, and inflammatory disorders.

Ischemic stroke, which accounts for 83% of all stroke cases (the remaining 17% are of the hemorrhagic-type) occurs in approximately 700,000 Americans each year, which equates to roughly 1 stroke every 45 seconds. Ischemic strokes occur as a result of an obstruction within a blood vessel supplying blood to the brain. The underlying condition for this type of obstruction is the development of fatty deposits lining the vessel walls, called atherosclerosis. These fatty deposits can cause two types of obstruction: 1) cerebral thrombosis, which refers to a thrombus (blood clot) that develops at the clogged part of the vessel and 2) cerebral embolism, which refers generally to a blood clot that forms at another location in the circulatory system, usually the heart and large arteries of the upper chest and neck. A portion of the blood clot breaks loose, enters the bloodstream and travels through the brain's blood vessels until it reaches vessels too small to let it pass. Current therapies to treat ischemic stroke are limited. To date, the only approved drug for ischemic stroke is recombinant tissue plasminogen activator (rt-PA). rt-PA, which acts as a thrombolytic, has a limited therapeutic window of opportunity (3 hours), therefore allowing only 1-2% of all stroke patients to receive treatment. There are no marketed neuroprotectants agents for ischemic stroke.

Parkinson's disease (PD) is a neurodegenerative disease that is neuropathologically characterized by the selective degeneration of dopaminergic (DAergic) neurons of the substantia nigra. PD is a progressive disease with a mean age at onset of 55, although 15% of patients are diagnosed before the age of 50. It is estimated that 1.5 million Americans have PD. Some of the classical signs of PD are resting tremor on one side of the body, generalized slowness of movement (bradykinesia), stiffness of limbs (rigidity), gait or balance problems (postural dysfunction). Current PD medications treat symptoms, whereas none prevent or retard DAergic neuron degeneration.

Given their clinical importance, prototypical molecules that clearly exhibit both neuroprotective and/or neuroregenerative activities have been highly sought after. Neurotrophins are a family of proteins that have extraordinary therapeutic properties in pre-clinical models of neurodegeneration. Although experimentally promising, clinical development of neurotrophins was met with severe obstacles and setbacks, such as the inability to deliver these large proteins to target population of neurons, instability of the proteins, and non-specific activity.

What is needed in the art are further compounds useful in treating neurological, proliferative, and inflammatory disorders.

SUMMARY OF THE INVENTION

In one aspect, the present invention provides novel compounds useful in treating, and in the preparation of medicaments useful in the treatment of, neurological, proliferative, and inflammatory disorders.

In another aspect, the present invention provides novel neuroprotective, anti-proliferative, and anti-inflammatory agents.

In a further aspect, the present invention provides novel compounds useful in treating, and in the preparation of medicaments useful in the treatment of, benign or malignant neoplastic disease, carcinomas, and adenocarcinomas.

In another aspect, the present invention provides novel compounds useful in treating, and in the preparation of medicaments useful in the treatment of, inflammatory disorders, including without limitation, autoimmune disorders (e.g., lupus), skin inflammatory disorders, intestinal inflammatory disorders, asthma and atopic disorders, and transplant/graft rejection.

In yet a further aspect, the present invention provides rapamycin analogues, and pharmaceutically acceptable salts, prodrugs, and metabolites thereof.

In another aspect, the present invention provides methods of preparing rapamycin analogues.

In a further aspect, the present invention provides methods of treating neurological, proliferative, cardiovascular, and inflammatory disorders.

In still another aspect, the present invention provides methods of treating complications due to stoke or head trauma.

In yet a further aspect, the present invention provides methods of treating benign or malignant neoplastic disease, carcinomas, and adenocarcinomas.

In still another aspect, the present invention provides methods for treating inflammatory disorders, including without limitation, autoimmune disorders (e.g., lupus), skin inflammatory disorders, intestinal inflammatory disorders, asthma and atopic disorders, and transplant/graft rejection.

In another aspect, the present invention provides a vascular stent or shunt which has been coated or impregnated with a compound of the invention.

Other aspects and advantages of the present invention are described further in the following detailed description of the preferred embodiments thereof.

DETAILED DESCRIPTION OF THE INVENTION

Figure 1:
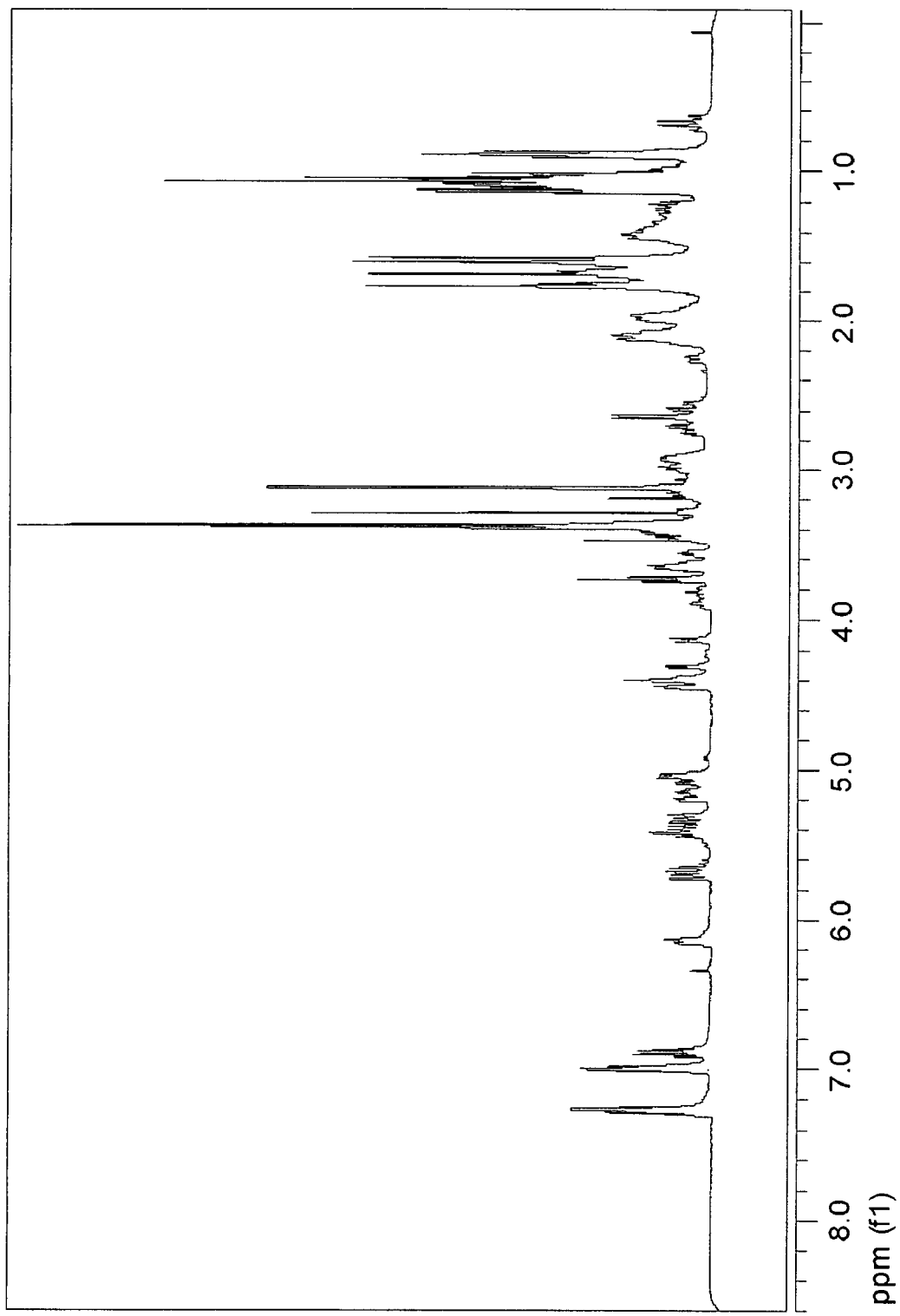
FIG. 1 provides the nuclear magnetic resonance (NMR) spectra for the compound of Example 1. The NMR spectra were obtained in $d_3$-acetonitrile using a 400 MHz spectrometer.

The present invention provides novel rapamycin analogues which are useful as neuroprotective, anti-proliferative, and/or anti-inflammatory agents. The novel rapamycin analogues have heteroatom substituents at the 1 and 4 positions of the rapamycin backbone. In another embodiment, the present invention provides rapamycin analogues having a cyclic structure at the 1, 2, 3 and/or 4 positions of the rapamycin backbone.

These novel compounds of the invention are useful as neuroprotective agents in compositions for use in treating neurological disorders. The neurological disorder, including, e.g., a neurodegenerative or neuromuscular degenerative condition, can be a result of a genetic disorder present at birth, a disorder developed during the lifespan of an individual, e.g., stroke, and/or the result of physical trauma, e.g., head, spinal injury, or injury to the peripheral nervous system.

Thus, a compound of the invention may be useful in ameliorating the symptoms of a pre-existing neurological disorder, preventing further neuro- and/or neuromuscular degeneration. In some embodiments, the neuroprotective agents of the invention can be used to delay the onset of symptoms associated with a neurological disorder.

The novel compounds of the present invention are also useful as anti-proliferative and anti-inflammatory agents and are thus useful in the treatment of inflammatory disorders, including autoimmune disorders, arthritic disorders, skin inflammatory disorders, intestinal inflammatory disorders, asthma and atopic disorders, and transplant/graft rejection.

It has surprisingly been found that at least two compounds of the invention, e.g., 9,27-dihydroxy-3-{2-[4-hydroxy-3-methoxycyclohexyl]-1-methylethyl}-10,21-dimethoxy-6,8,12,14,20,26-hexamethyl-37-phenyl 4,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentriacontine-1,5,11,28,29(6H,31H)-pentone and 37-(4-chloro-3-methylphenyl)-9,27-dihydroxy-3-{-2-[4-hydroxy-3-methoxycyclohexyl]-1-methylethyl}-10,21-dimethoxy-6,8,12,14,20,26-hexamethyl-,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentriacontine-1,5,11,28,29(6H,31H)-pentone; have anti-proliferative and immunosuppressive activity.

I. Compounds of the Invention

The present invention provides rapamycin analogues of the formula I:

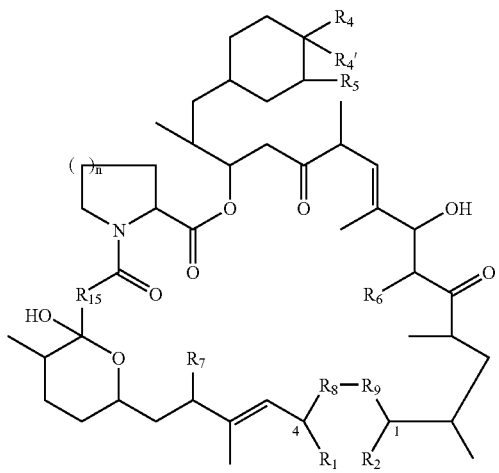

I $R_1$ and $R_2$ in the above-noted formula are different, independent groups and are selected from among $OR_3$ and $N(R_{3'})(R_{3''})$ or $R_1$ and $R_2$ are different, are connected through a single bond, and are selected from O and $NR_3$. $R_3$, $R_{3'}$, and $R_{3''}$ are independently selected from among H, $C_1$ to $C_6$ alkyl, $C_1$ to $C_6$ substituted alkyl, $C_3$ to $C_8$ cycloalkyl, substituted $C_3$ to $C_8$ cycloalkyl, aryl, substituted aryl, heteroaryl, and substituted heteroaryl. $R_4$ and $R_{4'}$ are (a) independently selected from among H, OH, O($C_1$ to $C_6$ alkyl), O(substituted $C_1$ to $C_6$ alkyl), O(acyl), O(aryl), O(substituted aryl), and halogen; or (b) taken together to form a double bond to O. $R_5$, $R_6$, and $R_7$ are independently selected from among H, OH, and $OCH_3$. $R_8$ and $R_9$ are connected through a (i) single bond and are $CH_2$ or (ii) double bond and are CH. $R_{15}$ is selected from among C=O, CHOH, and $CH_2$ and n is 1 or 2; or pharmaceutically acceptable, salts, prodrugs, or metabolites thereof.

In further embodiments, $R_1$ and $R_2$ are connected through a single bond and are selected from O and $NR_3$. In still a further embodiment, $R_1$ is O and $R_2$ is $NR_3$.

In one embodiment, $R_{3'}$ or $R_{3''}$ is an aryl or substituted aryl group, or a substituted benzene ring. In another embodiment, substituted benzene groups at $R_{3'}$ or $R_{3''}$ include rings of the following structure:

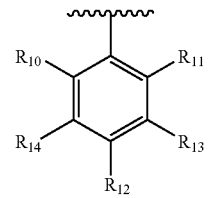

$R_{10}$, $R_{11}$, $R_{12}$, $R_{13}$, and $R_{14}$ are independently selected from among H, $C_1$ to $C_6$ alkyl, substituted $C_1$ to $C_6$ alkyl, aryl, substituted aryl, heteroaryl, substituted heteroaryl, halogen, acyl, OH, O(alkyl), O(substituted alkyl), O(aryl), O(substituted aryl), O(acyl), $NH_2$, NH(alkyl), NH(substituted alkyl), NH(aryl), NH(substituted aryl), and NH(acyl).

In further embodiments, $R_3$, $R_{3'}$ or $R_{3''}$ are phenyl optionally substituted by 1 or 2 substituents selected from $C_1$ to $C_6$ alkyl and halogen. In still further embodiments, $R_3$, $R_{3'}$ or $R_{3''}$ are phenyl optionally substituted with 1 or 2 methyl or chloro substituents, e.g. phenyl and 3-methyl, 4-chlorophenyl.

In one embodiment, $R_4$ or $R_{4'}$ are OH or O(acyl), e.g., where the acyl is —C(O)— optionally substituted alkyl, in particular where alkyl can be straight or branched and optionally substituted e.g. by heterocyclic such as aromatic heterocyclic such as pyridyl. An example is:

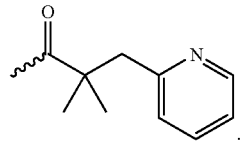

In other embodiments, rapamycin analogues of formula I include those where $R_5$, $R_6$ and $R_7$ are $OCH_3$, those where the nitrogen containing ring at positions 17-22 of the rapamycin backbone is a piperidine ring, or where $R_{15}$ is a carbonyl.

In one embodiment, the invention provides compounds of the following formula Ia:

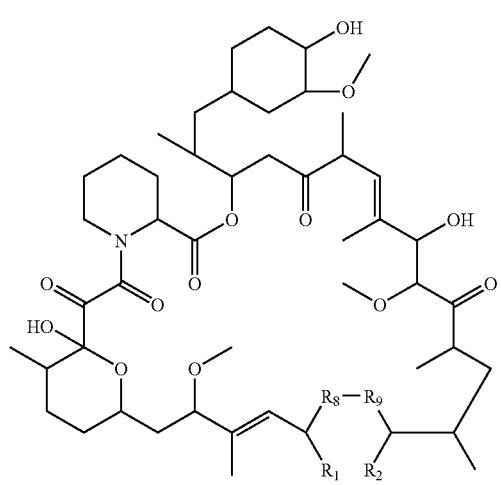

Ia where $R_1$, $R_2$, $R_8$, and $R_9$ are defined as noted above.

In another embodiment, the invention provides compounds of the following formula Ib:

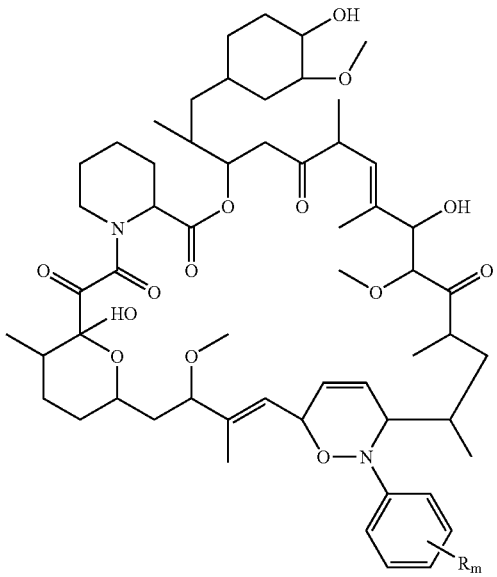

In formula Ib, R is independently selected from among H, $C_1$ to $C_6$ alkyl, substituted $C_1$ to $C_6$ alkyl, aryl, substituted aryl, heteroaryl, substituted heteroaryl, halogen, acyl, OH, O(alkyl), O(substituted alkyl), O(aryl), O(substituted aryl), O(acyl), $NH_2$, NH(alkyl), NH(substituted alkyl), NH(aryl), NH(substituted aryl), and NH(acyl) and m is 1 to 5.

Specific compounds of the invention are illustrated herein and include 9,27-dihydroxy-3-{2-[4-hydroxy-3-methoxycyclohexyl]-1-methylethyl}-10,21-dimethoxy-6,8,12,14,20,26-hexamethyl-37-phenyl-4,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentriacontine-1,5,11,28,29(6H,31H)-pentone; 9,27-dihydroxy-3-{2-[4-hydroxy-3-methoxycyclohexyl]-1-methylethyl}-10,21-dimethoxy-6,8,12,14,20,26-hexamethyl-37-phenyl-4,9,10,12,13,14,15,16,17,18,21,22,23,24,25,26,27,32,33,34,34a-henicosahydro-3H-23,27-epoxy-18,15-(epoxyimino)pyrido[2,1-c][1,4]oxazacyclohentriacontine-1,5,11,28,29(6H,31H)-pentone; 37-(4-chloro-3-methylphenyl)-9,27-dihydroxy-3-{-2-[4-hydroxy-3-methoxycyclohexyl]-1-methylethyl}-10,21-dimethoxy-6,8,12,14,20,26-hexamethyl-4,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentriacontine-1,5,11,28,29(6H,31H)-pentone; 37-(2,6-dichlorophenyl)-9,27-dihydroxy-3-{2-[4-hydroxy-3-methoxycyclohexyl]-1-methylethyl}-10,21-dimethoxy-6,8,12,14,20,26-hexamethyl-4,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentriacontine-1,5,11,28,29(6H,31H)-pentone; 9,27-dihydroxy-3-{-2-[4-hydroxy-3-methoxycyclohexyl]-1-methylethyl}-10,21-dimethoxy-6,8,12,14,20,26-hexamethyl-37-phenyl-4,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentriacontine-1,5,11,28,29(6H,31H)-pentone ester with -2,2-dimethyl-3-(pyridin-2-yl)-propionic acid; 37-(2,6-dichlorophenyl)-9,27-dihydroxy-3-{-2-[4-hydroxy-3-methoxycyclohexyl]-1-methylethyl}-10,21-dimethoxy-6,8,12,14,20,26-hexamethyl-4,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentriacontine-1,5,11,28,29(6H,31H)-pentone; or pharmaceutically acceptable, salts, prodrugs, or metabolites thereof. The invention is not limited to these illustrative compounds.

In another embodiment, the specific compounds include the following:

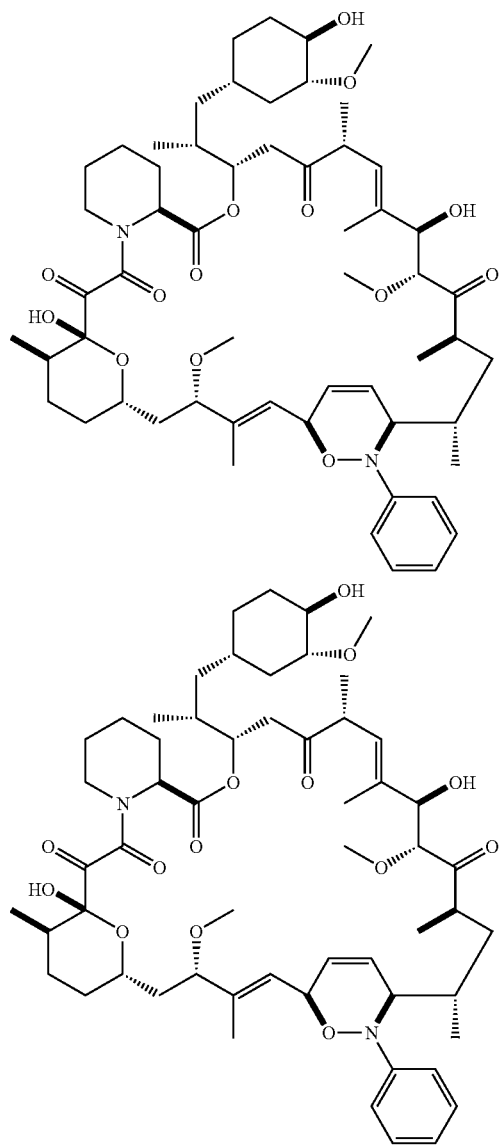

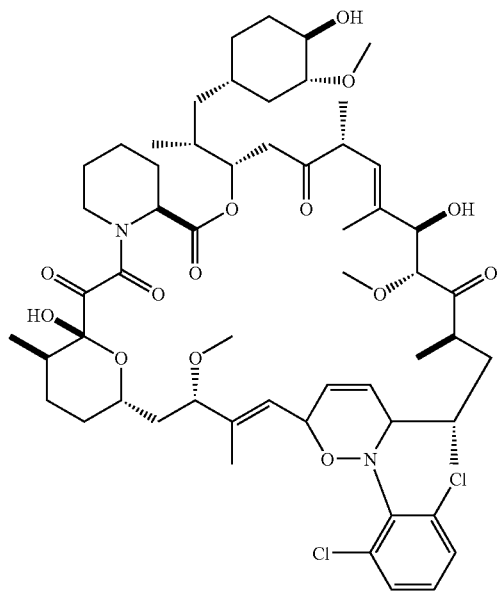

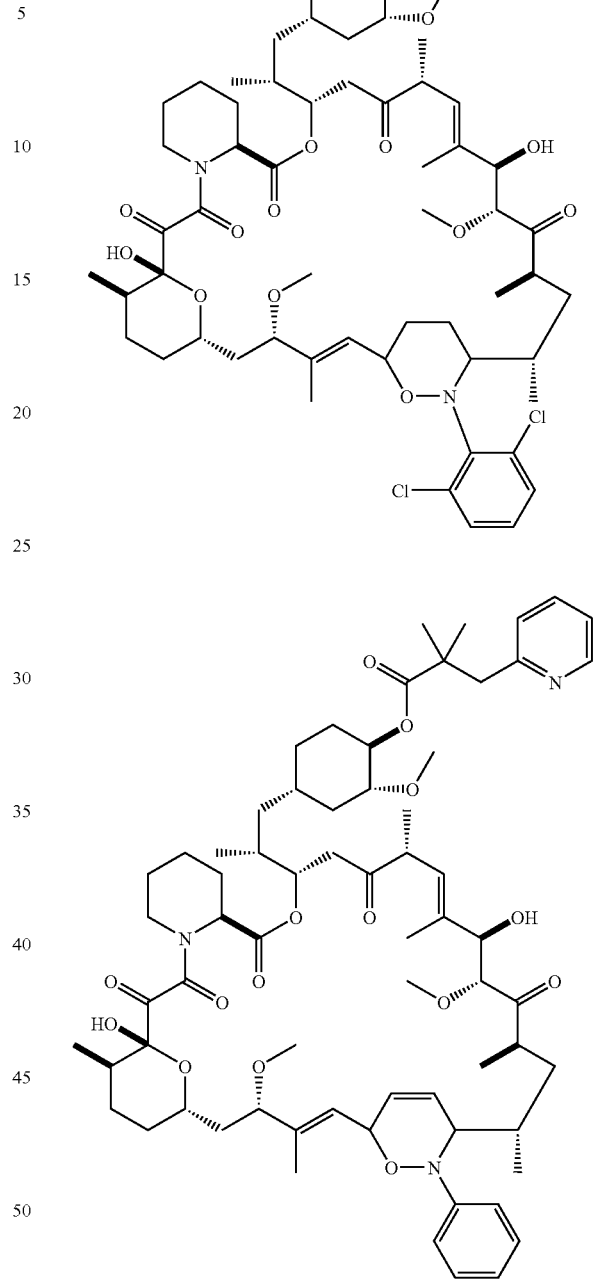

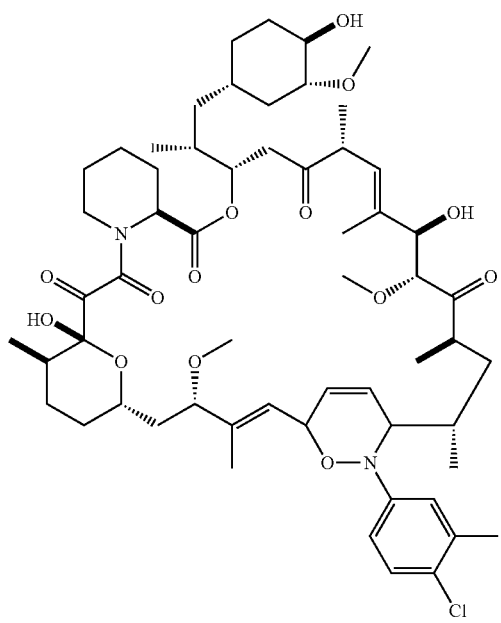

The present invention also provides a compound where $R_1$ and $R_2$ are connected through a single bond; $R_1$ is O; $R_2$ is $NR_3$; $R_3$ is phenyl; $R_4$ is OH; $R_5$-$R_7$ are $OCH_3$; and $R_8$ and $R_9$ are HC=CH; a compound where $R_1$ is $OR_3$; $R_2$ is $N(R_{3'})(R_{3''})$; $R_3$ is H; $R_{3'}$ is H; $R_{3''}$ is phenyl; $R_4$ is OH; $R_5$-$R_7$ are $OCH_3$; and $R_8$ and $R_9$ are $H_2C$—$CH_2$; a compound where $R_1$ and $R_2$ are connected through a single bond; $R_1$ is O; $R_2$ is $NR_3$; $R_3$ is phenyl; $R_4$ is OH; $R_5$-$R_7$ are $OCH_3$; and $R_8$ and $R_9$ are $H_2C$—$CH_2$; a compound where $R_1$ and $R_2$ are connected through a single bond; $R_1$ is O; $R_2$ is $NR_3$; $R_4$ is OH; $R_5$-$R_7$ are $OCH_3$; $R_8$ and $R_9$ are HC=CH; and $R_3$ is

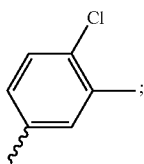

a compound where $R_1$ and $R_2$ are connected through a single bond; $R_1$ is O; $R_2$ is $NR_3$; $R_4$ is OH; $R_5$-$R_7$ are $OCH_3$; $R_8$ and $R_9$ are HC=CH; and $R_3$ is

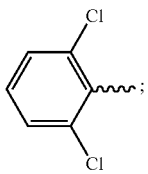

a compound where $R_1$ and $R_2$ are connected through a single bond; $R_1$ is O; $R_2$ is $NR_3$; $R_3$ is phenyl; $R_5$-$R_7$ are $OCH_3$; $R_8$ and $R_9$ are HC=CH; and $R_4$ is

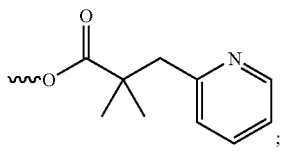

and a compound where $R_1$ and $R_2$ are connected through a single bond; $R_1$ is O; $R_2$ is $NR_3$; $R_4$ is OH; $R_5$-$R_7$ are $OCH_3$; $R_8$ and $R_9$ are $H_2C-CH_2$; and $R_3$ is

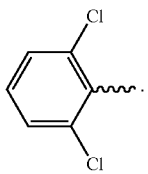

The compounds of the invention can contain one or more asymmetric carbon atoms and some of the compounds can contain one or more asymmetric (chiral) centers and can thus give rise to optical isomers and diastereomers. While shown without respect to stereochemistry, when the compounds can contain one or more chiral centers, preferably at least one of the chiral centers is of S-stereochemistry. Thus, the invention includes such optical isomers and diastereomers; as well as the racemic and resolved, enantiomerically pure stereoisomers; as well as other mixtures of the R and S stereoisomers, and pharmaceutically acceptable salts, hydrates, metabolites, and prodrugs thereof.

The term "alkyl" is used herein to refer to both straight- and branched-chain saturated aliphatic hydrocarbon groups having 1 to 10 carbon atoms, and desirably about 1 to 8 carbon atoms. The term "alkenyl" is used herein to refer to both straight- and branched-chain alkyl groups having one or more carbon-carbon double bonds and containing about 2 to 10 carbon atoms. In one embodiment, the term alkenyl refers to an alkyl group having 1 or 2 carbon-carbon double bonds and having 2 to about 6 carbon atoms. The term "alkynyl" group is used herein to refer to both straight- and branched-chain alkyl groups having one or more carbon-carbon triple bond and having 2 to 8 carbon atoms. In another embodiment, the term alkynyl refers to an alkyl group having 1 or 2 carbon-carbon triple bonds and having 2 to 6 carbon atoms.

The term "cycloalkyl" is used herein to refer to an alkyl group as previously described that is cyclic in structure and has about 4 to 10 carbon atoms, or about 5 to 8 carbon atoms.

The terms "substituted alkyl", "substituted alkenyl", and "substituted alkynyl" refer to alkyl, alkenyl, and alkynyl groups, respectively, having one or more substituents including, without limitation, halogen, CN, OH, $NO_2$, amino, aryl, heterocyclic, alkoxy, aryloxy, alkylcarbonyl, alkylcarboxy, and arylthio, which groups can be optionally substituted e.g. by 1 to 4 substituents including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio. These substituents can be attached to any carbon of an alkyl, alkenyl, or alkynyl group provided that the attachment constitutes a stable chemical moiety.

The term "aryl" as used herein refers to an aromatic system, e.g., of 6-20 carbon atoms, which can include a single ring or multiple aromatic rings fused or linked together (e.g. two or three) where at least one part of the fused or linked rings forms the conjugated aromatic system. The aryl groups can include, but are not limited to, phenyl, naphthyl, biphenyl, anthryl, tetrahydronaphthyl, phenanthryl, indene, benzonaphthyl, fluorenyl, and carbazolyl.

The term "substituted aryl" refers to an aryl group which is substituted with one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. In one embodiment, a substituted aryl group is substituted with 1 to 4 substituents including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio.

The term "heterocyclic" as used herein refers to a stable 4- to 7-membered monocyclic or multicyclic heterocyclic ring which is saturated, partially unsaturated, or wholly unsaturated, including aromatic such as pyridyl. The heterocyclic ring has carbon atoms and one or more heteroatoms including nitrogen, oxygen, and sulfur atoms. In one embodiment, the heterocyclic ring has 1 to 4 heteroatoms in the backbone of the ring. When the heterocyclic ring contains nitrogen or sulfur atoms in the backbone of the ring, the nitrogen or sulfur atoms can be oxidized. The term "heterocyclic" also refers to multicyclic rings, e.g., of 9 to 20 ring members in which a heterocyclic ring is fused to an aryl ring. The heterocyclic ring can be attached to the aryl ring through a heteroatom or carbon atom, provided the resultant heterocyclic ring structure is chemically stable.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Oxygen-containing rings include, but are not limited to, furyl, tetrahydrofuranyl, pyranyl, pyronyl, and dioxinyl rings. Nitrogen-containing rings include, without limitation, pyrrolyl, pyrazolyl, imidazolyl, triazolyl, pyridyl, piperidinyl, 2-oxopiperidinyl, pyridazinyl, pyrimidinyl, pyrazinyl, piperazinyl, azepinyl, triazinyl, pyrrolidinyl, and azepinyl rings. Sulfur-containing rings include, without limitation, thienyl and dithiolyl rings. Mixed heteroatom containing rings include, but are not limited to, oxathiolyl, oxazolyl, thiazolyl, oxadiazolyl, oxatriazolyl, dioxazolyl, oxathiazolyl, oxathiolyl, oxazinyl, oxathiazinyl, morpholinyl, thiamorpholinyl, thiamorpholinyl sulfoxide, oxepinyl, thiepinyl, and diazepinyl rings. Fused heteroatom-containing rings include, but are not limited to, benzofuranyl, thionapthene, indolyl, benazazolyl, purindinyl, pyranopyrrolyl, isoindazolyl, indoxazinyl, benzoxazolyl, anthranilyl, benzopyranyl, quinolinyl, isoquinolinyl, benzodiazonyl, naphthylridinyl, benzothienyl, pyridopyridinyl, benzoxazinyl, xanthenyl, acridinyl, and purinyl rings.

The term "substituted heterocyclic" as used herein refers to a heterocyclic group having one or more substituents including halogen, CN, OH, $NO_2$, amino, alkyl, cycloalkyl, alkenyl, alkynyl, alkoxy, aryloxy, alkyloxy, alkylcarbonyl, alkylcarboxy, aminoalkyl, and arylthio, which groups can be optionally substituted. In one embodiment, a substituted heterocyclic group is substituted with 1 to 4 substituents.

The term "acyl" refers to a —C(O)— group, which is substituted at the carbon atom. The acyl group can be substituted or a terminal acyl group such as an HC(O)- group. The substituents can include any substituents noted above for alkyl groups, viz. one or more substituents including, without limitation, halogen, CN, OH, $NO_2$, amino, aryl, heterocyclic, alkoxy, aryloxy, alkylcarbonyl, alkylcarboxy, and arylthio, which groups can be optionally substituted. Examples include —C(O)-alkoxy (e.g. —OMe or —OEt) or —C(O)-alkyl where alkyl can be straight or branched and optionally substituted e.g., by heterocyclic (such as pyridyl).

The term "alkoxy" as used herein refers to the O(alkyl) group, where the point of attachment is through the oxygen-atom and the alkyl group is optionally substituted.

The term "aryloxy" as used herein refers to the O(aryl) group, where the point of attachment is through the oxygen-atom and the aryl group is optionally substituted.

The term "alkyloxy" as used herein refers to the alkylOH group, where the point of attachment is through the alkyl group.

The term "arylthio" as used herein refers to the S(aryl) group, where the point of attachment is through the sulfur-atom and the aryl group can be optionally substituted.

The term "alkylcarbonyl" as used herein refers to the C(O)(alkyl) group, where the point of attachment is through the carbon-atom of the carbonyl moiety and the alkyl group is optionally substituted.

The term "alkylcarboxy" as used herein refers to the C(O)O(alkyl) group, where the point of attachment is through the carbon-atom of the carboxy moiety and the alkyl group is optionally substituted.

The term "aminoalkyl" as used herein refers to both secondary and tertiary amines where the point of attachment is through the nitrogen-atom and the alkyl groups are optionally substituted. The alkyl groups can be the same or different. The term "halogen" as used herein refers to Cl, Br, F, or I groups.

II. Methods of Preparing the Compounds of the Invention

The rapamycin analogues of formula I of the present invention are prepared from a rapamycin starting material. Preferably, the rapamycin starting material includes, without limitation, rapamycin, norrapamycin, deoxorapamycin, desmethylrapamycins, or desmethoxyrapamycin, or pharmaceutically acceptable salts, prodrugs, or metabolites thereof. However, one of skill in the art would readily be able to select a suitable rapamycin starting material that can be utilized to prepare the novel rapamycin analogues of the present invention.

The term "desmethylrapamycin" refers to the class of rapamycin compounds which lack one or more methyl groups. Examples of desmethylrapamycins that can be used according to the present invention include 3-desmethylrapamycin (U.S. Pat. No. 6,358,969), 7-O-desmethyl-rapamycin (U.S. Pat. No. 6,399,626), 17-desmethylrapamycin (U.S. Pat. No. 6,670,168), and 32-O-desmethylrapamycin, among others.

The term "desmethoxyrapamycin" refers to the class of rapamycin compounds which lack one or more methoxy groups and includes, without limitation, 32-desmethoxyrapamycin.

The rapamycin analogues of formula I of the present invention are therefore prepared by combining a rapamycin starting material and a dienophile. The term "dienophile" refers to a molecule that reacts with a 1,3-diene to give a [4+2] cycloaddition product. Preferably, the dienophile utilized in the present invention is an optionally substituted nitrosobenzene. A variety of nitrosobenzenes can be utilized in the present invention and include nitrosobenzene, 2,6-dichloronitrosobenzene, and 1-chloro-2-methyl-4-nitrosobenzene, among others. One of skill in the art would readily be able to select the amount of nitrosobenzene that would be effective in preparing the rapamycin analogues of the present invention. Preferably, an excess of the nitrosobenzene is utilized, and more preferably in a 5:1 ratio of nitrosobenzene to rapamycin starting material. However, even a 1:1, 2:1, or 3:1 ratio of nitrosobenzene to rapamycin can be utilized as determined by one of skill in the art.

The nitrosobenzene and rapamycin starting material is combined in a solvent. The solvent preferably dissolves the nitrosobenzene and/or rapamycin on contact, or dissolves the nitrosobenzene and rapamycin as the reaction proceeds. Solvents that can be utilized in the present invention include, without limitation, dimethylformamide, dioxane such as p-dioxane, chloroform, alcohols such as methanol and ethanol, ethyl acetate, water, acetonitrile, tetrahydrofuran, dichloromethane, and toluene, or combinations thereof. However, one of skill in the art would readily be able to select a suitable solvent based upon the solubility of the rapamycin starting material and nitrosobenzene, as well as the reactivity of the solvent with the same. The amount of solvent utilized depends upon the scale of the reaction and specifically the amount of rapamycin starting material and nitrosobenzene present in the reaction mixture. One of skill in the art would readily be able to determine the amount of solvent required.

Typically, the solution containing the nitrosobenzene, rapamycin starting material, and solvent is maintained at elevated temperatures, and preferably a temperature that does not promote decomposition of the rapamycin and nitrosobenzene. In one embodiment, the solution is maintained a temperature of about 30 to about 70° C., and preferably about 50° C. The components are heated for a period of time sufficient to permit reaction between the rapamycin and nitrosobenzene. One of skill in the art using known techniques would readily be able to monitor the progress of the reaction during heating and thereby determine the amount of time required to perform the reaction. In one preferred embodiment, the rapamycin and nitrosobenzene are combined with p-dioxane and maintained at a temperature of about 50° C.

Isolation and purification of the rapamycin analogue is well within one of skill in the art and include chromatography including, without limitation, and recrystallization, high performance liquid chromatography (HPLC) such as reverse phase HPLC, and normal phase HPLC, and size-exclusion chromatography.

Once the rapamycin analogue is obtained, it can be reduced to form a more saturated rapamycin analogue. One of skill in the art would readily be able to select a suitable reducing agent for use in the present invention. Preferably, reduction of the rapamycin analogue can be effected using a hydrogenation agent. One of skill in the art would readily be able to select a suitable hydrogenation agent for use in the present invention. Typically, transition metal catalysts or transition metals on a support, preferably a carbon support, among others, in the presence hydrogen gas, are utilized to carry out the reduction. In a preferred embodiment, the reduction is performed using palladium metal on carbon in the presence of hydrogen gas.

Reduction of the rapamycin analogue is typically carried out in a solvent. A variety of solvents can be utilized in the reduction and include, without limitation, alcohols such as methanol. However, one of skill in the art would readily be able to select a suitable solvent for use in the present invention and depending on the hydrogenation catalyst and rapamycin analogue being reduced. The amount of solvent depends on the scale of the reaction, and specifically the amount of rapamycin analogue being reduced.

The amount of hydrogenation agent utilized in the present invention can readily be determined by one of skill in the art. However, one of skill in the art would be able to determine and adjust the amount of hydrogenation agent necessary to perform the reduction and to form the more saturated rapamycin analogues of the present invention. Further, a variety of apparatuses can be utilized to perform the hydrogenation of the present invention and include Parr apparatuses, among others. The selection of the particular apparatus for the hydrogenation is well within one of skill in the art.

A preferred method of preparing the rapamycin analogues of the present invention is summarized in Scheme 1 below:

Scheme 1

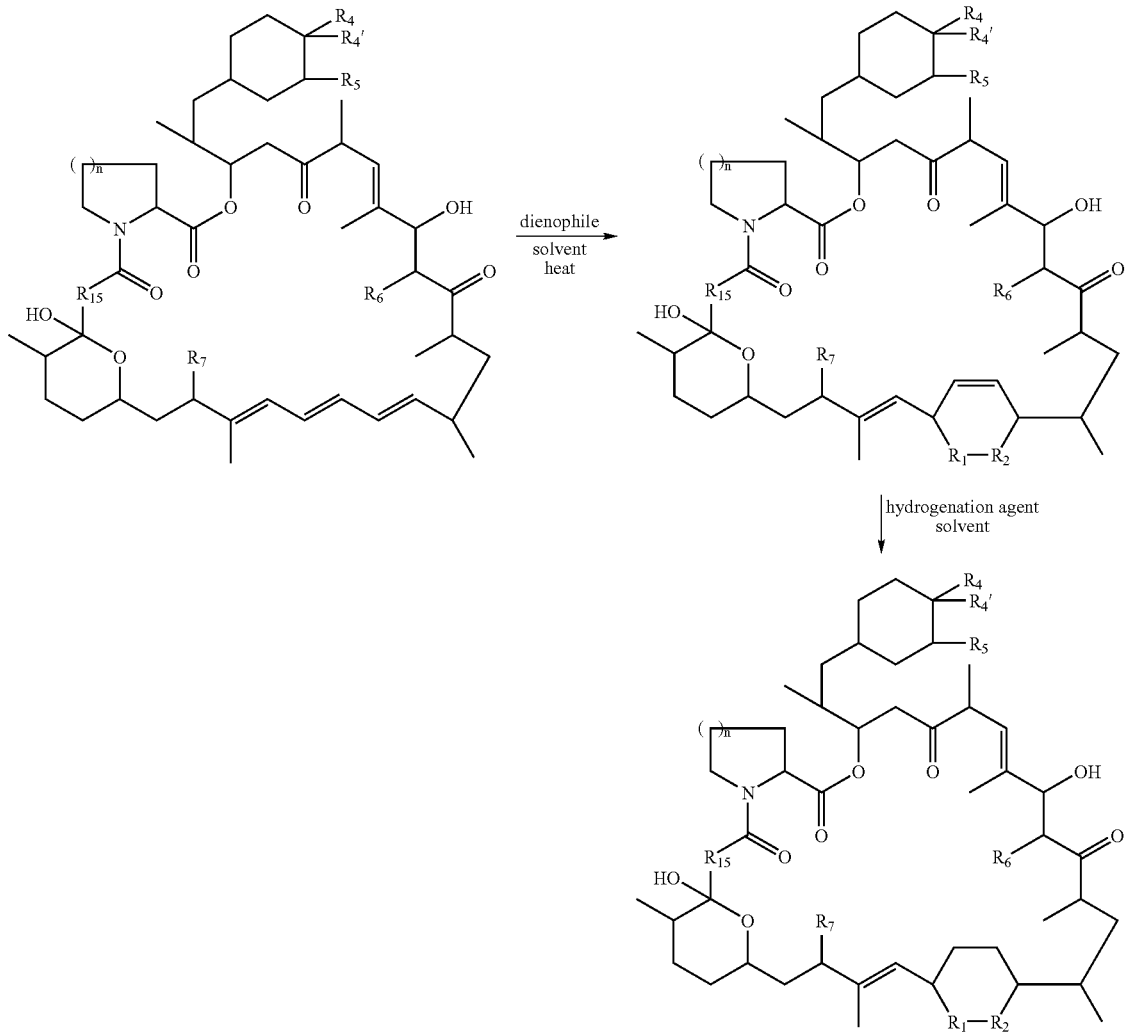

where $R_1$, $R_2$, $R_4$, $R_{4'}$, $R_6$, $R_7$, $R_{15}$, and n are defined above.

The rapamycin analogues of the present invention can be utilized in the form of pharmaceutically acceptable salts, prodrugs, or metabolites thereof derived from pharmaceutically or physiologically acceptable acids or bases. These salts include, but are not limited to, the following salts with mineral or inorganic acids such as hydrochloric acid, sulfuric acid, nitric acid, phosphoric acid and organic acids such as acetic acid, oxalic acid, succinic acid, and maleic acid. Other salts include salts with alkali metals or alkaline earth metals, such as sodium, potassium, calcium or magnesium in the form of esters, carbamates and other conventional "pro-drug" forms, which, when administered in such form, convert to the active moiety in vivo.

III. Methods of Using the Compounds of the Present Invention

The rapamycin analogues of formulae I, Ia, and Ib of the present invention, including the more and less saturated rapamycin analogues, are useful in applications relating to neurological disorders (including neuromuscular disorders) and cardiovascular disorders, among others. The rapamycin analogues of formulae I, Ia, and Ib of the present invention, including the more and less saturated rapamycin analogues, are useful in disorders involving the dysfunction of calcium ($Ca^{2+}$) ion channels, such as ryanodine receptor (RyR1, RyR2, and Ryr3) channelopathies including, among others, malignant hyperthermia, central core disease, cathecolaminergic polymorphic ventricular tachycardia, and arrhythmogenic right ventricular dysplasia type 2 (ARVD-2). The rapamycin analogues of formulae I, Ia, and Ib of the present invention, including the more and less saturated rapamycin analogues, are also useful in dihydropyridine receptor channelopathies, including those resultant from ryanodine receptor activity due to the activity of dihydropyridine-sensitive calcium ion ($Ca^{2+}$) channels. As used herein, the term "channelopathy" refers to a disease or disorder involving dysfunction of an ion channel.

The diseases and disorders referred to herein are grouped herein under conventional headings, e.g., neurological disorders and inflammatory disorders. One of skill in the art will recognize that the diseases or disorders referred to herein may be appropriately grouped under different headings or under multiple headings. The grouping of diseases and/or disorders referred to herein is not a limitation of the present invention.

The compounds of the present invention are useful in treating neurological disorders including Alzheimer's disease; epilepsy; Huntington's Disease; Parkinson's Disease; stroke; spinal cord injury; traumatic brain injury; Lewy body dementia; Pick's disease; Niewmann-Pick disease; amyloid angiopathy; cerebral amyloid angiopathy; systemic amyloidosis; hereditary cerebral hemorrhage with amyloidosis of the Dutch type; inclusion body myositis; mild cognitive impairment; Down's syndrome; and neuromuscular disorders including amyotrophic lateral sclerosis (ALS), multiple sclerosis, and muscular dystrophies including Duchenne dystrophy, Becker muscular dystrophy, Facioscapulohumeral (Landouzy-Dejerine) muscular dystrophy, and limb-girdle muscular dystrophy (LGMD); and in the preparation of medicaments therefor. The rapamycin analogues are also useful in treating complications due to stroke, head trauma, or spinal injury, or other injuries to the brain, peripheral nervous, central nervous, or neuromuscular system, and in the preparation of medicaments therefor.

The novel rapamycin analogues are also useful as neuroprotective agents. The rapamycin analogues of the present invention may also be useful as neuroregenerative agents, i.e., restoring some neurological and/or neuromuscular or other function following onset of one of the above conditions and/or injury, stroke, or other trauma.

The compounds of the present invention are useful in treating cardiovascular disorders including, but not limited to: congestive heart failure; arrhythmogenic syndromes, including paroxysomal tachycardia, delayed afterdepolarizations, ventricular tachycardia, sudden tachycardia, exercise-induced arrhythmias, long QT syndromes, and bidirectional tachycardia; thromboembolic disorders, including arterial cardiovascular thromboembolic disorders, venous cardiovascular thromboembolic disorders, and thromboembolic disorders in the chambers of the heart; atherosclerosis; restenosis; peripheral arterial disease; coronary bypass grafting surgery; carotid artery disease; arteritis; myocarditis; cardiovascular inflammation; vascular inflammation; coronary heart disease (CHD); unstable angina (UA); unstable refractory angina; stable angina (SA); chronic stable angina; acute coronary syndrome (ACS); first or recurrent myocardial infarction; acute myocardial infarction (AMI); myocardial infarction; non-Q wave myocardial infarction; non-STE myocardial infarction; coronary artery disease; ischemic heart disease; cardiac ischemia; ischemia; ischemic sudden death; transient ischemic attack; stroke; peripheral occlusive arterial disease; venous thrombosis; deep vein thrombosis; thrombophlebitis; arterial embolism; coronary arterial thrombosis; cerebral arterial thrombosis; cerebral embolism; kidney embolism; pulmonary embolism; thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis; thrombosis resulting from atherosclerosis, surgery or surgical complications, prolonged immobilization, arterial fibrillation, congenital thrombophilia, cancer, diabetes, effects of medications or hormones, and complications of pregnancy; cardiac arrhytmias including supraventricular arrhythmias, atrial arrhythmias, atrial flutter, atrial fibrillation; other diseases listed in Heart Disease: A Textbook of Cardiovascular Medicine, 2 Volume Set, 6th Edition, 2001, Eugene Braunwald, Douglas P. Zipes, Peter Libby, Douglas D. Zipes; and in the preparation of medicaments therefor.

In a further embodiment, the cardiovascular disease is: atherosclerosis; coronary heart disease (CHD); restensosis; peripheral arterial disease; coronary bypass grafting surgery; carotid artery disease; arteritis; myocarditis; cardiovascular inflammation; vascular inflammation; unstable angina (UA); unstable refractory angina; stable angina (SA); chronic stable angina; acute coronary syndrome (ACS); myocardial infarction; or acute myocardial infarction (AMI), including first or recurrent myocardial infarction, non-Q wave myocardial infarction, non-ST-segment elevation myocardial infarction and ST-segment elevation myocardial infarction.

In still a further embodiment, the cardiovascular disease is: atherosclerosis; coronary heart disease (CHD); unstable angina (UA); unstable refractory angina; stable angina (SA); chronic stable angina; acute coronary syndrome (ACS); myocardial infarction; or acute myocardial infarction (AMI), including first or recurrent myocardial infarction, non-Q wave myocardial infarction, non-ST-segment elevation myocardial infarction and ST-segment elevation myocardial infarction.

The rapamycin analogues of formulae I, Ia, and Ib of the present invention have also been shown to have immunosuppressive activity, and thus are useful as anti-inflammatory agents for treating inflammatory disorders, including without limitation, autoimmune disorders (e.g., lupus), skin inflammatory disorders, intestinal inflammatory disorders, asthma and atopic disorders, and transplant/graft rejection. The rapamycin analogues are therefore useful in the treatment of inflammatory disorders, and in the preparation of medicaments therefor, including without limitation, autoimmune disorders, e.g., systemic lupus erythematosis (SLE), arthritic disorders (e.g., rheumatoid arthritis, psoriatic arthritis, osteoarthritis, ankylosing spondylatis), diabetes mellitus (type I), multiple sclerosis, myasthenia gravis, vasculitis; skin inflammatory disorders (e.g., psoriasis, dermatitis and scleroderma); intestinal inflammatory disorders (e.g., inflammatory bowel disease (IBD), Crohn's disease and ulcerative colitis); asthma and atopic disorders (e.g., allergy); and transplant/graft rejection and graft v. host disease.

These compounds of formulae I, Ia, and Ib are also useful in treating or preventing benign or malignant neoplastic disease or carcinomas and adenocarcinomas, and in the preparation of medicaments therefor. One such compound is 9,27-dihydroxy-3-{2-[4-hydroxy-3-methoxycyclohexyl]-1-methylethyl}-10,21-dimethoxy-6,8,12,14,20,26-hexamethyl-37-phenyl-4,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentriacontine-1,5,11,28,29(6H,31H)-pentone. Another such compound is 37-(4-chloro-3-methylphenyl)-9,27-dihydroxy-3-{-2-[4-hydroxy-3-methoxycyclohexyl]-1-methylethyl}-10,21-dimethoxy-6,8,12,14,20,26-hexamethyl-4,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentriacontine-1,5,11,28,29(6H,31H)-pentone. Carcinomas and adenocarcinomas that can be treated according to the present invention include, without limitation, carcinomas or adenocarcinomas of the endometrium, ovary, breast, colon, renal, prostate, pituitary, meningioma or other hormone-dependent tumors.

The dosage requirements of the rapamycin analogues of the present invention can vary depending on the condition, severity of the symptoms presented and the particular subject being treated. One of skill in the art would readily be able to determine the amount of the rapamycin analogue required. In one embodiment, about 0.5 to 200 mg is administered. In a further embodiment, about 0.5 to 100 mg is administered. In another embodiment, about 0.5 to about 75 mg is administered. In yet a further embodiment, about 1 to about 25 mg is administered. In another embodiment, about 0.5 to about 10 mg is administered, particularly when used in combination with another agent. In yet a further embodiment, about 2 to about 5 mg is administered. In yet another embodiment, about 5 to about 15 mg is administered. Treatment can be initiated with dosages of the rapamycin analogue smaller than those required to produce a desired effect and generally less than the optimum dose of the rapamycin analogue. Thereafter, the dosage can be increased until the optimum effect under the circumstances is reached. Precise dosages will be determined by the administering physician based on experience with the individual subject being treated. In general, the compositions of this invention are most desirably administered at a concentration that will generally afford effective results without causing any harmful or deleterious side effects.

IV. Methods of Preparing Administrable Compositions Containing the Rapamycin Analogues In one aspect, the present invention includes methods of preparing a pharmaceutical composition containing one or more rapamycin analogues of the present invention. As used herein, reference to compositions containing "a rapamycin analogue" or "the rapamycin analogue" of the invention are intended to encompass compositions containing one or more rapamycin analogues of the invention. The composition can be administered to a mammalian subject by several different routes and is desirably administered orally in solid or liquid form.

Solid forms, including tablets, capsules, and caplets, containing the rapamycin analogue can be formed by blending the rapamycin analogue with one or more of the components described above. In one embodiment, the components of the composition are dry or wet blended. In another embodiment, the components are dry granulated. In a further embodiment, the components are suspended or dissolved in a liquid and added to a form suitable for administration to a mammalian subject.

Liquid forms containing the rapamycin analogue can be formed by dissolving or suspending the rapamycin analogue in a liquid suitable for administration to a mammalian subject.

Compositions containing the rapamycin analogue of the present invention can be prepared according to the present invention by combining the rapamycin analogue and a pharmaceutically acceptable carrier.

The compositions described herein containing the rapamycin analogue can be formulated in any form suitable for the desired route of delivery using a pharmaceutically effective amount of the rapamycin analogue. For example, the compositions of the invention can be delivered by a route such as oral, dermal, transdermal, intrabronchial, intranasal, intravenous, intramuscular, subcutaneous, parenteral, intraperitoneal, intranasal, vaginal, rectal, sublingual, intracranial, epidural, intratracheal, or by sustained release. Preferably, delivery is oral.

The oral dosage tablet composition of this invention can also be used to make oral dosage tablets containing derivatives of the rapamycin analogue, including, but not limited to, esters, carbamates, sulfates, ethers, oximes, carbonates, and the like which are known to those of skill in the art.

A pharmaceutically effective amount of the rapamycin analogue can vary depending on the specific compound(s), mode of delivery, severity of the condition being treated, and any other active ingredients used in the composition. The dosing regimen can also be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. However, daily dosages can be lowered or raised based on the periodic delivery.

The rapamycin analogues of the present invention can be combined with one or more pharmaceutically acceptable carriers or excipients including, without limitation, solid and liquid carriers which are compatible with the compositions of the present invention. Such carriers include adjuvants, syrups, elixirs, diluents, binders, lubricants, surfactants, granulating agents, disintegrating agents, emollients, metal chelators, pH adjustors, surfactants, fillers, disintegrants, and combinations thereof, among others. In one embodiment, the rapamycin analogue is combined with metal chelators, pH adjustors, surfactants, fillers, disintegrants, lubricants, and binders.

Adjuvants can include, without limitation, flavoring agents, coloring agents, preservatives, and supplemental antioxidants, which can include vitamin E, ascorbic acid, butylated hydroxytoluene (BHT) and butylated hydroxyanisole (BHA).

Binders can include, without limitation, cellulose, methylcellulose, hydroxymethylcellulose, carboxymethylcellulose calcium, carboxymethylcellulose sodium, hydroxypropylcellulose, hydroxypropylmethylcellulose phthalate, microcrystalline cellulose, noncrystalline cellulose, polypropylpyrrolidone, polyvinylpyrrolidone (povidone, PVP), gelatin, gum arabic and acacia, polyethylene glycols, starch, sugars such as sucrose, kaolin, dextrose, and lactose, cholesterol, tragacanth, stearic acid, gelatin, casein, lecithin (phosphatides), cetostearyl alcohol, cetyl alcohol, cetyl esters wax, dextrates, dextrin, glyceryl monooleate, glyceryl monostearate, glyceryl palmitostearate, polyoxyethylene alkyl ethers, polyoxyethylene castor oil derivatives, polyoxyethylene stearates, polyvinyl alcohol, and gelatin, among others. In one embodiment, the binder is povidone, hydroxypropylmethylcellulose, carboxymethylcellulose, or gelatin. In another embodiment, the binder is povidone.

Lubricants can include magnesium stearate, light anhydrous silicic acid, talc, stearic acid, sodium lauryl sulfate, and sodium stearyl furamate, among others. In one embodiment, the lubricant is magnesium stearate, stearic acid, or sodium stearyl furamate. In another embodiment, the lubricant is magnesium stearate.

Granulating agents can include, without limitation, silicon dioxide, microcrystalline cellulose, starch, calcium carbonate, pectin, crospovidone, and polyplasdone, among others.

Disintegrating agents or disintegrants can include croscarmellose sodium, starch, carboxymethylcellulose, substituted hydroxypropylcellulose, sodium bicarbonate, calcium phosphate, calcium citrate, sodium starch glycolate, pregelatinized starch or crospovidone, among others. In one embodiment, the disintegrant is croscarmellose sodium.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants can include polysorbates, sorbitan esters, poloxamer, or sodium lauryl sulfate. In one embodiment, the surfactant is sodium lauryl sulfate.

Metal chelators can include physiologically acceptable chelating agents including edetic acid, malic acid, or fumaric acid. In one embodiment, the metal chelator is edetic acid.

pH adjusters can also be utilized to adjust the pH of a solution containing the rapamycin analogue to about 4 to about 6. In one embodiment, the pH of a solution containing the rapamycin analogue is adjusted to a pH of about 4.6. pH adjustors can include physiologically acceptable agents including citric acid, ascorbic acid, fumaric acid, or malic acid, and salts thereof. In one embodiment, the pH adjuster is citric acid.

Fillers that can be used according to the present invention include anhydrous lactose, microcrystalline cellulose, mannitol, calcium phosphate, pregelatinized starch, or sucrose. In one embodiment, the filler is anhydrous lactose. In another embodiment, the filler is microcrystalline cellulose.

In one embodiment, compositions containing the rapamycin analogue of the invention are delivered orally by tablet, caplet or capsule, microcapsules, dispersible powder, granule, suspension, syrup, elixir, and aerosol. Desirably, when compositions containing the rapamycin analogue are delivered orally, delivery is by tablets and hard- or liquid-filled capsules.

In another embodiment, the compositions containing the rapamycin analogue can be delivered intravenously, intramuscularly, subcutaneously, parenterally and intraperitoneally in the form of sterile injectable solutions, suspensions, dispersions, and powders which are fluid to the extent that easy syringe ability exits. Such injectable compositions are sterile and stable under conditions of manufacture and storage, and free of the contaminating action of microorganisms such as bacteria and fungi.

In a further embodiment, compositions containing the rapamycin analogue can be delivered rectally in the form of a conventional suppository.

In another embodiment, compositions containing the rapamycin analogue can be delivered vaginally in the form of a conventional suppository, cream, gel, ring, or coated intrauterine device (IUD).

In another embodiment, compositions containing the rapamycin analogue can be delivered via coating or impregnating of a supporting structure, i.e., a framework capable of containing of supporting pharmaceutically acceptable carrier or excipient containing a compound of the invention, e.g., vascular stents or shunts, coronary stents, peripheral stents, catheters, arterio-venous grafts, by-pass grafts, and drug delivery balloons for use in the vasculature. In one embodiment, coatings suitable for use include, but are not limited to, polymeric coatings composed of any polymeric material in which the compound of the invention is substantially soluble. Supporting structures and coating or impregnating methods, e.g., those described in U.S. Pat. No. 6,890,546, are known to those of skill in the art and are not a limitation of the present invention.

In yet another embodiment, compositions containing the rapamycin analogue can be delivered intranasally or intrabronchially in the form of an aerosol.

The rapamycin analogues are administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions are advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

The rapamycin analogues are also administered parenterally or intraperitoneally. Solutions or suspensions of these active compounds as a free base or pharmacologically acceptable salt are prepared in water suitably mixed with a surfactant such as hydroxypropylcellulose. Dispersions are also prepared in glycerol, liquid, polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form is sterile and fluid to the extent that easy syringe ability exits. It is stable under conditions of manufacture and storage and is preserved against the contaminating action of microorganisms such as bacterial and fungi. The carrier is a solvent or dispersion medium containing, for example, water, ethanol (e.g., glycerol, propylene glycol and liquid polyethylene glycol), suitable mixtures thereof, and vegetable oil.

V. Kits of the Invention

The present invention also provides kits or packages containing the rapamycin analogues. Kits of the present invention can include the rapamycin analogue of the present invention and a carrier suitable for administration to a mammalian subject as discussed above. The kits can also contain the reagents required to prepare the rapamycin analogues of the present invention and include a rapamycin, an optionally substituted nitrosobenzene, and a solvent.

The kits can optionally include other reagents to form other rapamycin analogues and include hydrogenation agents.

The kit can further contain instructions for performing the reactions of the present invention. Also provided in a kit can be other suitable chemicals, disposable gloves, decontamination instructions, applicator sticks or containers, and sample preparator cups.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

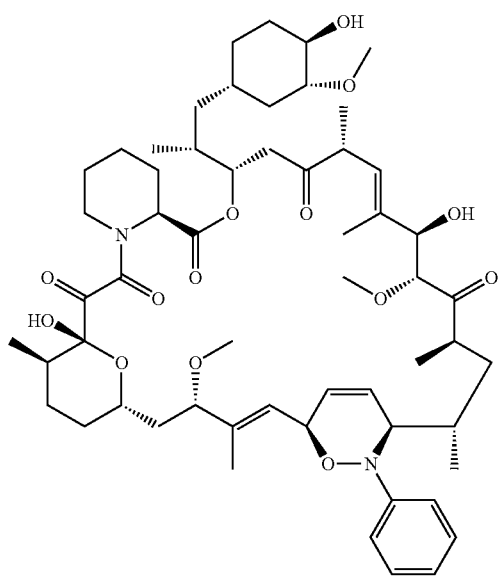

Table 1 provides the mass spectral (MS) data and FIG. 1 provides the nuclear magnetic resonance (NMR) spectrum for the compound produced by the following two alternative routes.

TABLE 1

Theoretical Neutral Mass: 1020.59226
Exact Mass High Resolution Results

| Adduct | Exptl. | Exact | mmu | ppm | RI % |
|---|---|---|---|---|---|
| $[M + H]^{1+}$ | 1021.59780 | 1021.59954 | −1.74 | −1.70 | 100.0 |
| $[M + Na]^{1+}$ | 1043.57740 | 1043.58148 | −4.08 | −3.91 | 17.8 |
| $[M + NH_4]^{1+}$ | 1038.62305 | 1038.62608 | −3.03 | −2.92 | 1.2 |
| $[M + 2H]^{2+}$ | 511.30109 | 511.30341 | −2.32 | −4.53 | 1.8 |
| $[M + CH_3OH + H]^{1+}$ | 1053.62596 | 1053.62575 | 0.21 | 0.20 | 1.5 |

A. Route 1

Rapamycin (2.5 g, 2.73 mmol) was dissolved in 200 mL p-dioxane. To this solution was added, dropwise, a solution of nitrosobenzene (1.50 g, 5 eq) in 200 mL p-dioxane. The reaction mixture was stirred at 50° C. for 64 hours, and then the products were chromatographed via reversed-phase high performance liquid chromatography (HPLC) (column: 200× 50 mm YMC ODS-A, mobile phase: 80% methanol:water, ramped flow rate from 10 mL/min to 35 mL/min in 10 minutes, then hold at 35 mL/min for an additional 65 minutes) to yield 1.22 g of the product (44% yield, $t_R$=12.1 min, analytical HPLC conditions: column=YMC ODS-A S-3 120 Å, mobile phase/gradient: 95% water (+0.025% formic acid)/ acetonitrile (+0.025% formic acid) to 5% water in 6 minutes, hold at 5% for 9 minutes, flow=0.30 mL/min).

B. Route 2—Alternate Route

Rapamycin (0.3 g, 0.328 mmol) was dissolved in 5 mL toluene with gentle heating. To this solution was added, dropwise, a solution of nitrosobenzene (0.1 g, 3 eq) in 5 mL toluene. The reaction mixture was stirred at 70° C. for 16 hours, and then the products were chromatographed via reversed-phase high performance liquid chromatography (HPLC) (column: 250×20 mm YMC ODS-A with 50×20 guard, mobile phase: 80 to 85% methanol:water in 40 minutes, flow=20 mL/min) to yield 0.139 g of the product (42% yield, $t_R$=12.1 min, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes, flow=0.30 mL/min).

Example 2

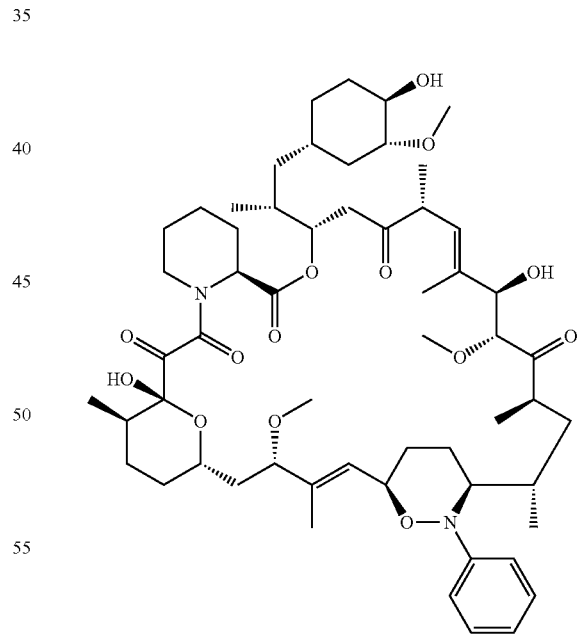

Figure 2:
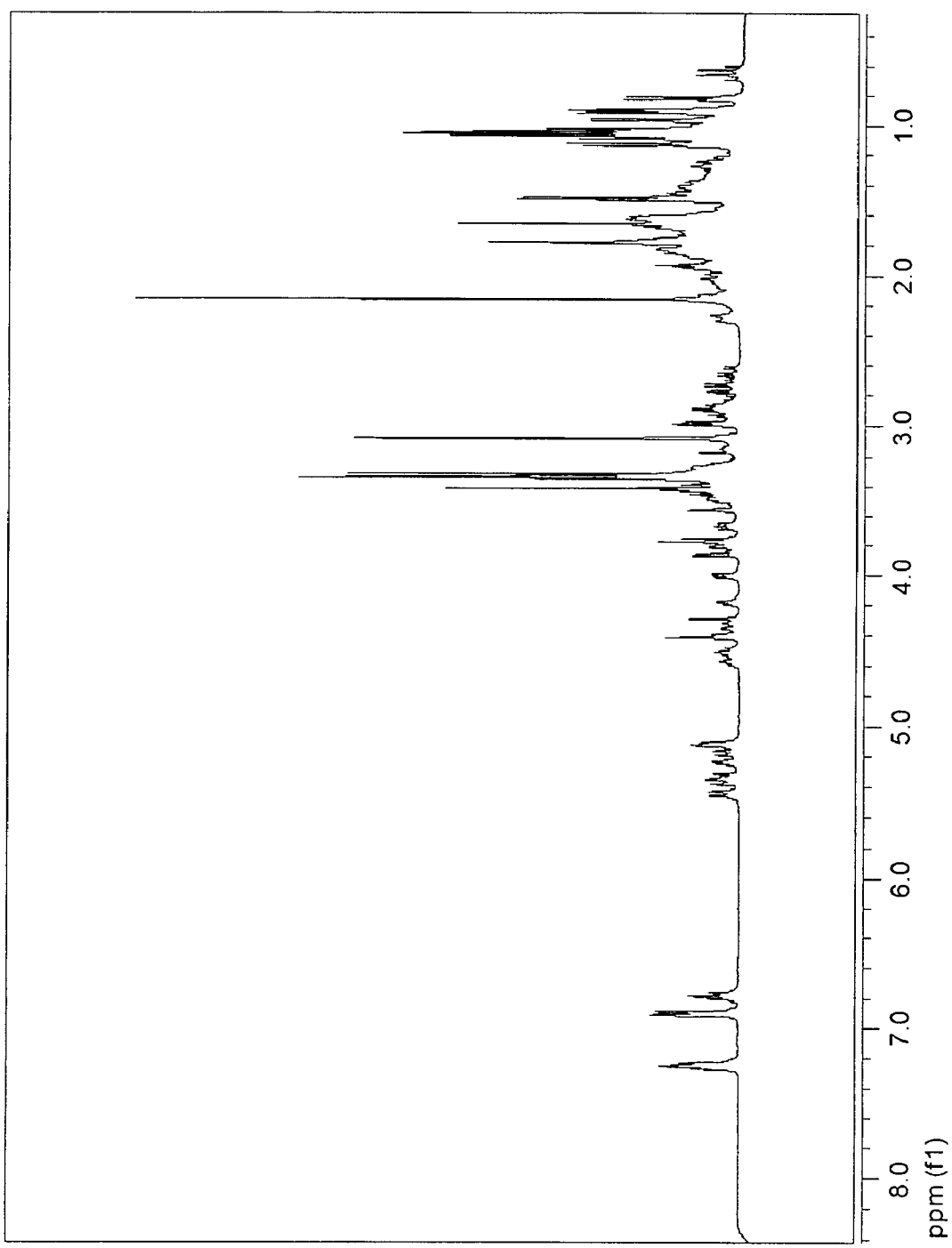
FIG. 2 provides the NMR spectra for the compound of Example 2. The NMR spectra were obtained in $d_3$-acetonitrile using a 400 MHz spectrometer.

Table 2 provides the mass spectral (MS) data and FIG. 2 provides the nuclear magnetic resonance (NMR) spectrum for the compound produced by the following two alternative routes.

A. Route 1

The compound prepared according to Example 1 (0.29 g, 0.284 mmol) was dissolved in 7 mL methanol in an 18 mm test-tube, and a spatula tip of Pd/C catalyst (Aldrich) was added. The mixture was hydrogenated on a Parr apparatus for 15 minutes at 2.0 atmosphere $H_2$. The products were chromatographed via reversed-phase HPLC (column: 250×20 mm YMC ODS-A with 50×20 guard, mobile phase: 80% methanol:water for 15 minutes, then to 85% in 5 minutes, then held at 85% for 20 minutes, flow=20 mL/min) to yield 0.089 g of the product (31% yield, $t_R$=12.6 min, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes, flow=0.30 mL/min)

B. Route 2—Alternate Route

The compound prepared according to Example 1 (9.85 g, 9.65 mmol) was dissolved in 50 mL methanol, and 3 spatula tips of Pd/C catalyst (Aldrich) was added. The mixture was hydrogenated on a Parr apparatus for 2.5 hours at 2.5 atmospheres $H_2$. The products were chromatographed via reversed-phase HPLC (column: 250×50 mm YMC ODS-A, mobile phase: 80% methanol:water for 40 minutes, then to 85% in 5 minutes, then held at 85% for 35 minutes, flow=35 mL/min) to yield 3.35 g of the product (15% yield, $t_R$=12.2 min, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes, flow=0.30 mL/min)

TABLE 2

| Theoretical Neutral Mass: 1022.60791 Exact Mass High Resolution Results | | | | | |
| --- | --- | --- | --- | --- | --- |
| Adduct | Exptl. | Exact | mmu | ppm | RI % |
| $[M + H]^{1+}$ | 1023.61722 | 1023.61519 | 2.03 | 1.99 | 100.0 |
| $[M + Na]^{1+}$ | 1045.59943 | 1045.59713 | 2.30 | 2.20 | 10.5 |

Example 3

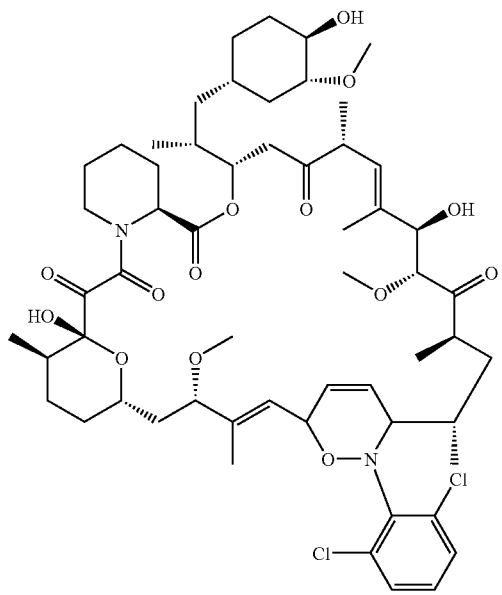

Figure 3:
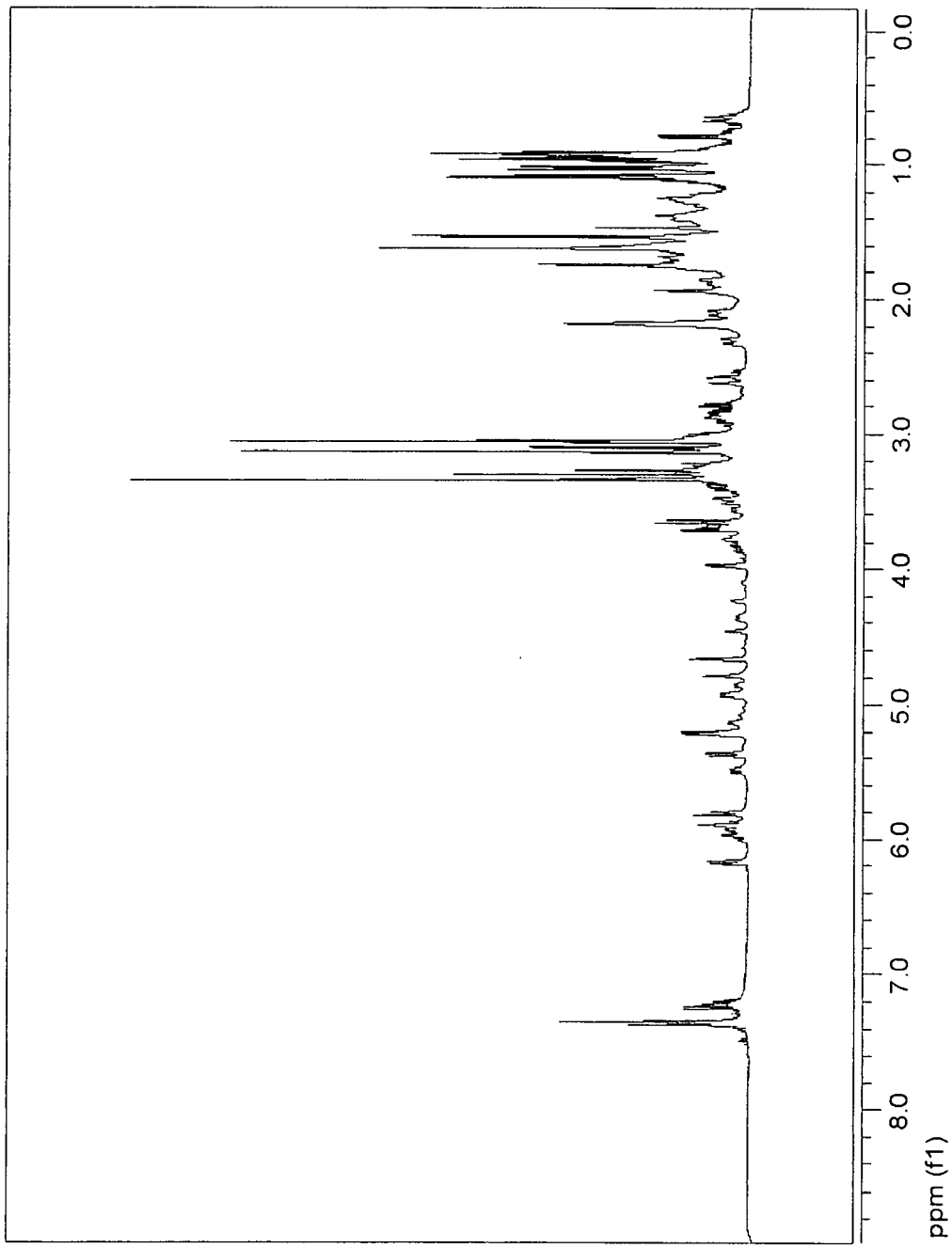
FIG. 3 provides the NMR spectra for the compound of Example 3. The NMR spectra were obtained in $d_3$-acetonitrile using a 400 MHz spectrometer.

Rapamycin (0.25 g, 0.274 mmol) was dissolved in 5 mL toluene with gentle heating. To this solution was added, dropwise, a solution of 2,6-dichloronitrosobenzene (0.144 g, 3 eq) in 7 mL toluene. The reaction mixture was stirred at 80° C. for 36 hours, and then the products were chromatographed via reversed-phase HPLC (column: 250×20 mm YMC ODS-A with 50×20 guard, mobile phase: 80 to 85% methanol:water in 40 minutes, flow=20 mL/min) to yield 0.046 g of the product (15% yield, $t_R$=13.0 minutes, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes, flow=0.30 mL/min). The MS data is provided in Table 3 and FIG. 3 provides the NMR spectrum.

TABLE 3

| Theoretical Neutral Mass: 1088.51431 Exact Mass High Resolution Results | | | | | |
| --- | --- | --- | --- | --- | --- |
| Adduct | Exptl. | Exact | mmu | ppm | RI % |
| $[M + H]^{1+}$ | 1089.52125 | 1089.52159 | −0.34 | −0.31 | 19.1 |
| $[M + Na]^{1+}$ | 1111.50044 | 1111.50353 | −3.09 | −2.78 | 18.1 |
| $[M + NH_4]^{1+}$ | 1106.54443 | 1106.54813 | −3.70 | −3.35 | 1.2 |

Example 4

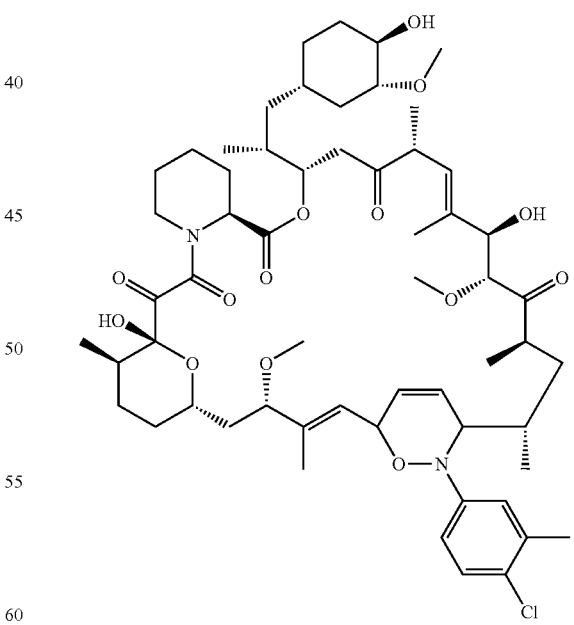

Figure 4:
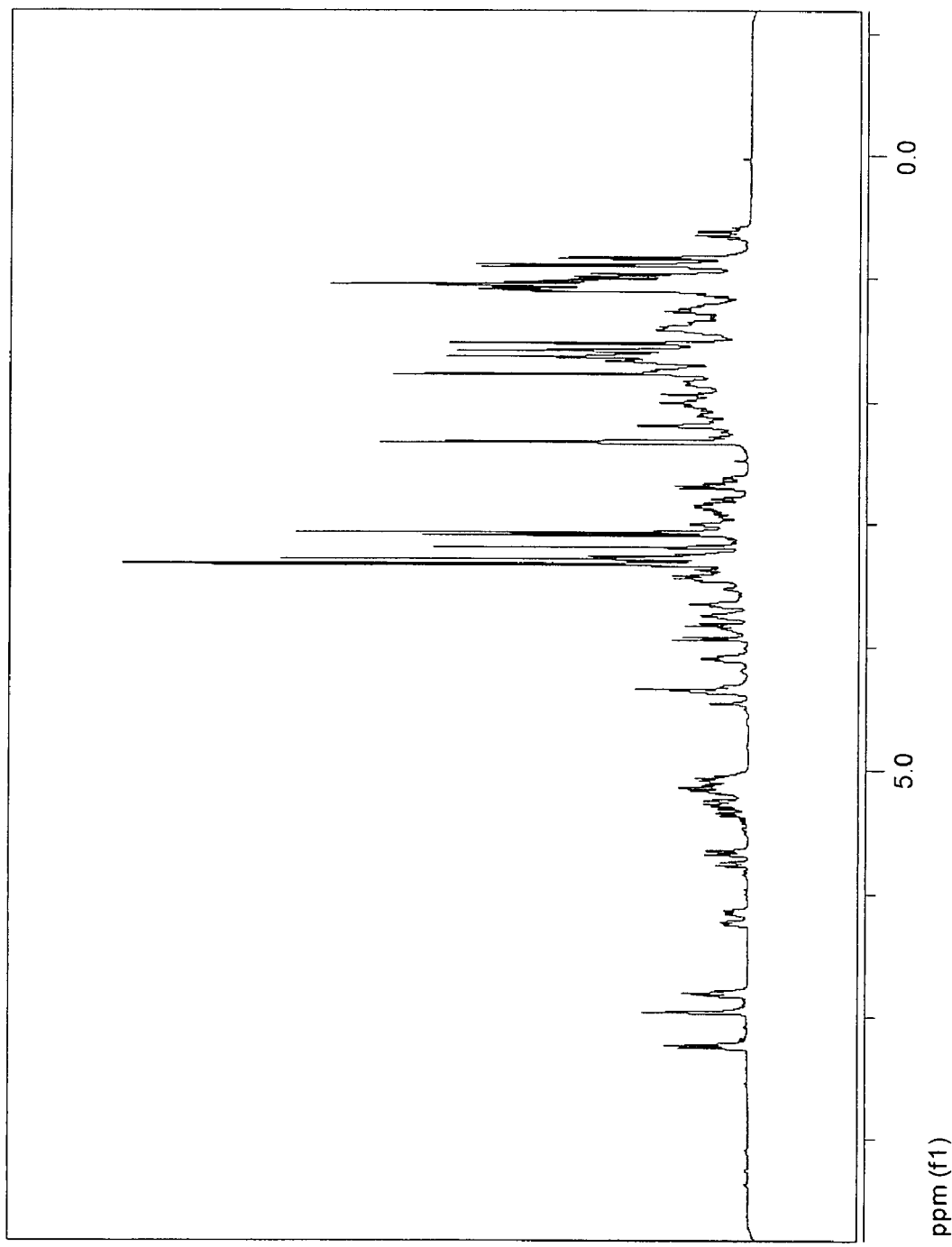
FIG. 4 provides the NMR spectra for the compound of Example 4. The NMR spectra were obtained in $d_3$-acetonitrile using a 400 MHz spectrometer.

The synthesis of this example was performed as described in Example 3 and employing 0.05 g of rapamycin and 0.042 g of 1-chloro-2-methyl-4-nitrosobenzene to give 0.012 g of the product (20% yield, $t_R$=12.8 min). The MS data is provided in Table 4 and FIG. 4 provides the NMR spectrum.

TABLE 4

| Experimental Mass | Elemental Formula (proposed) | Predicted Mass | Δ (mmu) | Δ (ppm) | Ion Assignment (proposed) |
|---|---|---|---|---|---|
| 1091.55815 | $C_{58}H_{85}ClN_2O_{14}Na^{1+}$ | 1091.55815 | 0.00 | 0.00 | $[M+Na]^{1+}$ |
| 936.54361 | $C_{51}H_{79}NO_{13}Na^{1+}$ | 936.54436 | −0.75 | −0.80 | $[M+Na]^{1+}$—$C_7H_6ClNO$ |

Example 5

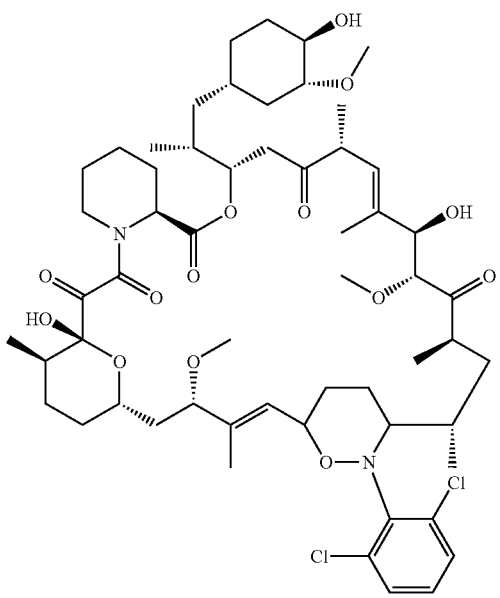

Figure 5:
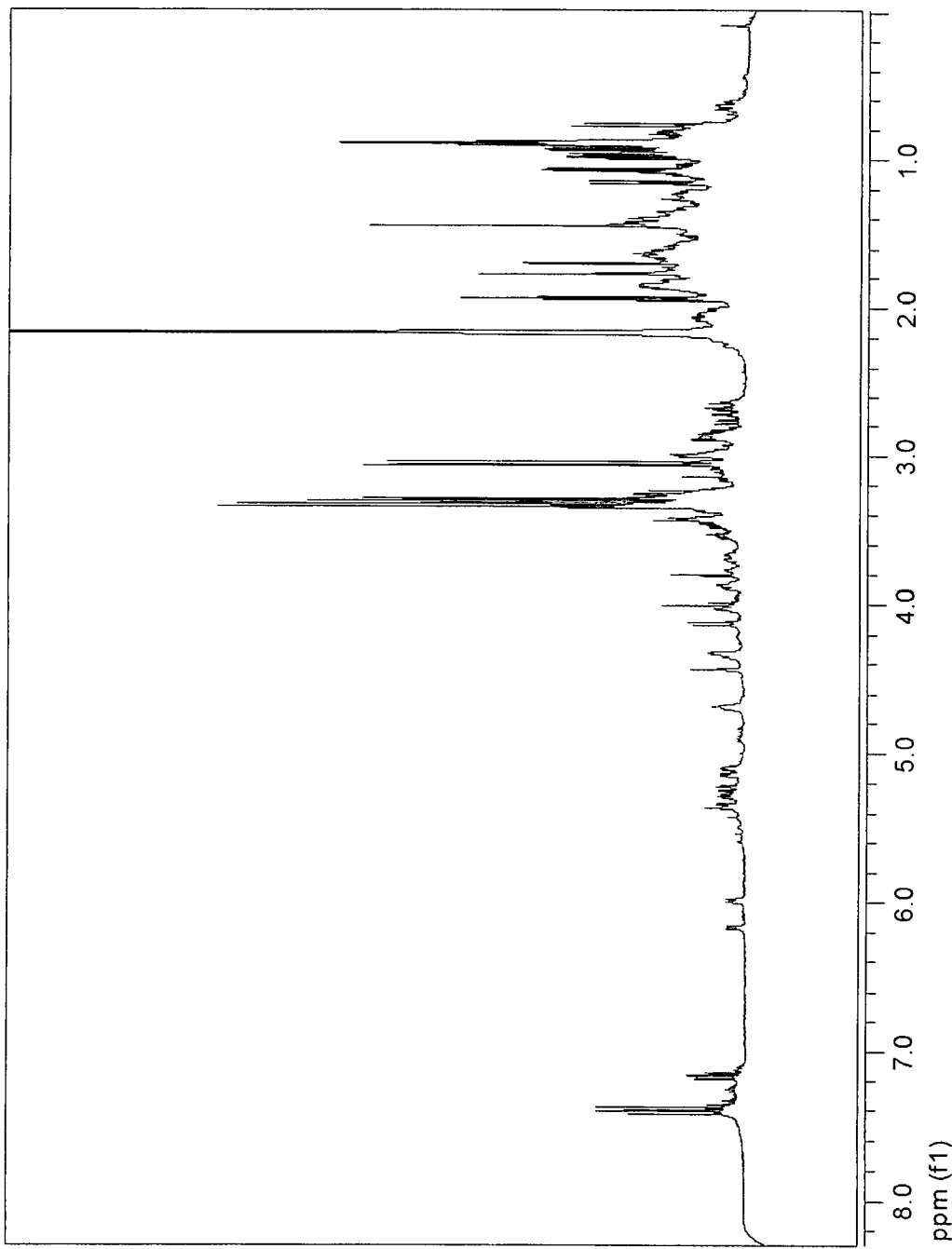
FIG. 5 provides the NMR spectra for the compound of Example 5. The NMR spectra were obtained in $d_3$-acetonitrile using a 400 MHz spectrometer.

The product from Example 3 (0.046 g, 0.0422 mmol) was dissolved in 5 mL methanol in an 18 mm test-tube, and a spatula tip of Pd/C catalyst (Aldrich) was added. The mixture was hydrogenated on a Parr apparatus for 60 minutes at 3 atmospheres $H_2$. The products were chromatographed via reversed-phase HPLC (column: 250×20 mm YMC ODS-A with 50×20 guard, mobile phase: 85% methanol:water to 90% in 15 minutes, then hold at 90% for 25 minutes, flow=20 mL/min) to yield 0.005 g of the product (11% yield, $t_R$=10.0 minutes, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes, flow=0.30 mL/min). The MS data is provided in Table 5 and FIG. 5 provides the NMR spectrum.

TABLE 5

Theoretical Neutral Mass: 1090.52996
Exact Mass High Resolution Results

| Adduct | Exptl. | Exact | mmu | ppm | RI % |
|---|---|---|---|---|---|
| $[M+H]^{1+}$ | 1091.53497 | 1091.53724 | −2.27 | −2.08 | 4.3 |
| $[M+Na]^{1+}$ | 1113.52166 | 1113.51918 | 2.48 | 2.23 | 4.8 |
| $[M+NH_4]^{1+}$ | 1108.56627 | 1108.56378 | 2.49 | 2.24 | 15.5 |

Example 6

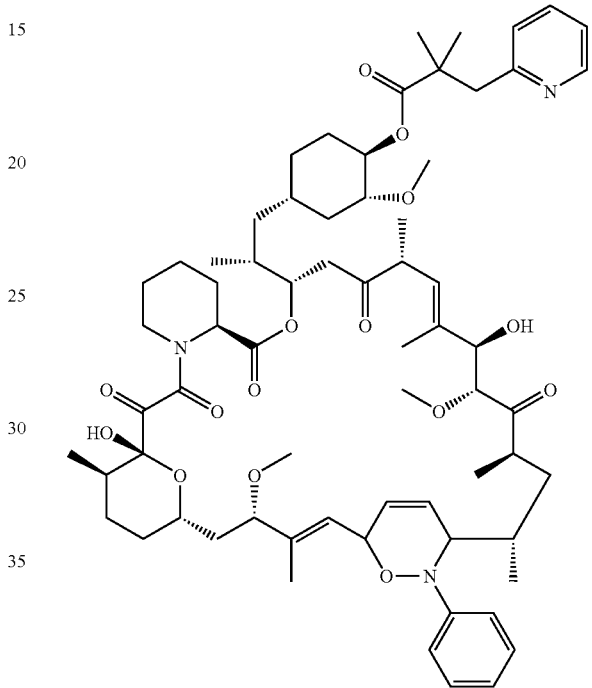

Figure 6:
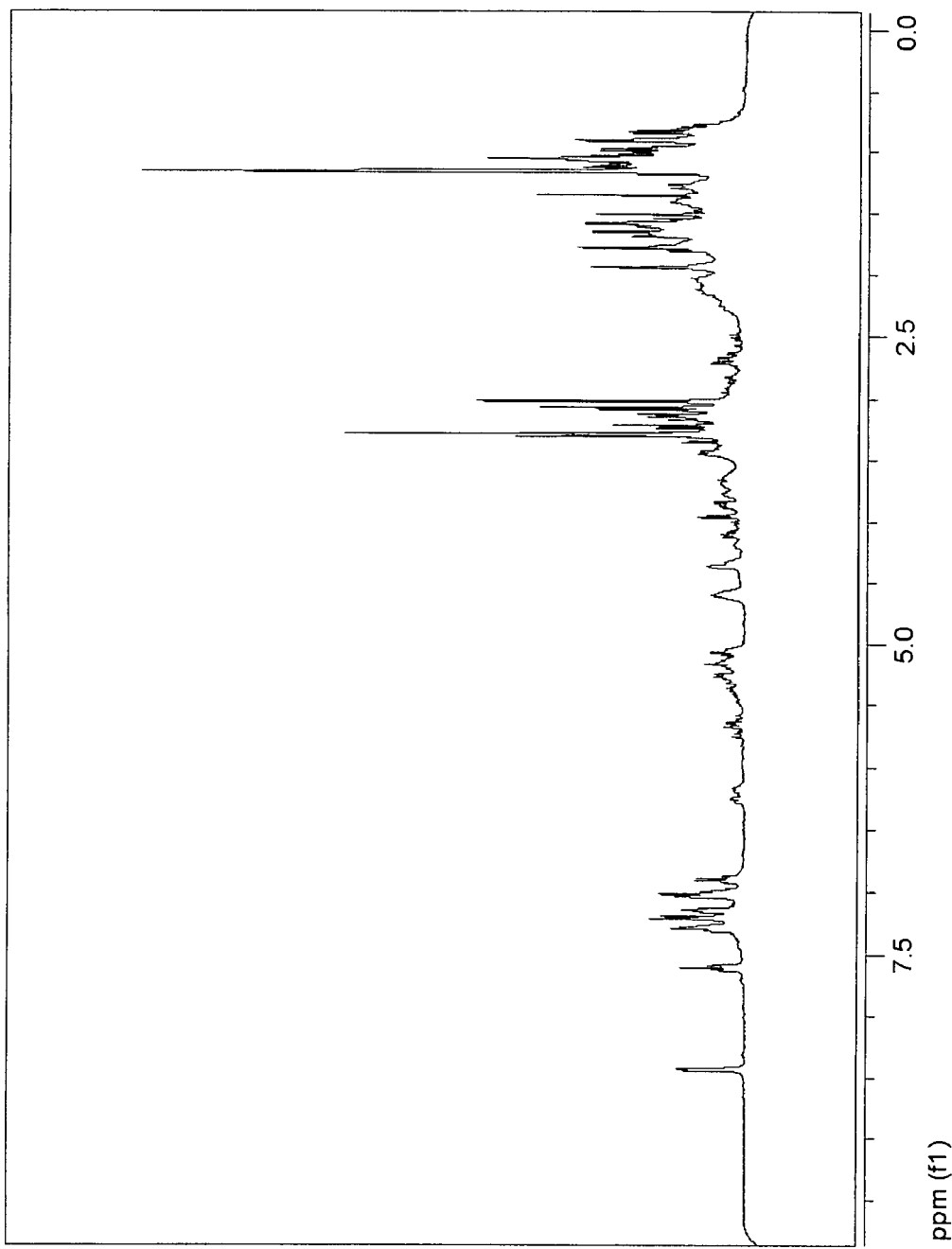
FIG. 6 provides the NMR spectra for the compound of Example 6. The NMR spectra were obtained in $d_3$-acetonitrile using a 400 MHz spectrometer.

The synthesis of this example was performed as described in Example 3 and using 0.108 g (0.099 mmol) rapamycin 42-ester with 2,2-dimethyl-3-(pyridine-2-yl)-propionic acid (prepared according to the method of U.S. Pat. No. 5,385, 908) and 0.032 g nitrosobenzene (0.297 mmol, 3 eq.). The reaction was stirred at 70 EC for 40 hours and then the products were chromatographed via reversed-phase HPLC (column: 250×20 mm YMC ODS-A with 50×20 guard, mobile phase: 80 to 85% methanol:water in 15 minutes, then to 90% methanol in 10 minutes, then hold at 90% for 15 minutes, flow=20 mL/min) to yield 0.007 g of the product (6% yield, $t_R$=13.0 minutes). The MS data is shown in Table 6 and FIG. 6 provides the NMR spectrum.

TABLE 6

Theoretical Neutral Mass: 1181.67632
Exact Mass High Resolution Results

| Adduct | Exptl. | Exact | mmu | ppm | RI % |
|---|---|---|---|---|---|
| $[M+H]^{1+}$ | 1182.68360 | 1182.68747 | 3.87 | 3.28 | 23.2 |
| $[M+2H]^{2+}$ | 591.84544 | 591.84715 | 1.71 | 2.90 | 79.6 |
| $[M+H+Na]^{2+}$ | 602.83641 | 602.83743 | 1.02 | 1.70 | 34.1 |

Example 7

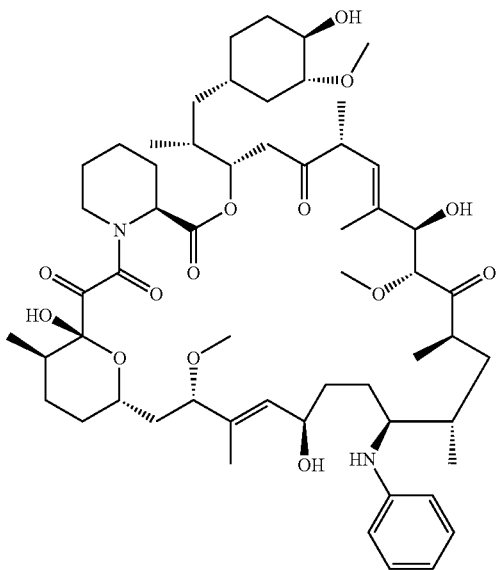

The compound prepared according to Example 1 (0.031 g, 0.03 mmol) was dissolved in 5 mL methanol in an 18 mm test-tube, and a spatula tip of Pd/C catalyst (Aldrich) was added. The mixture was hydrogenated on a Parr apparatus for 30 minutes at 2.0 atmosphere H2. The products were chromatographed via reversed-phase HPLC (column: 250×20 mm YMC ODS-A with 50×20 guard, mobile phase: 80% methanol:water for 15 minutes, then to 85% in 5 minutes, then held at 85% for 20 minutes, flow=20 mL/min) to yield 0.016 g of the product (55% yield, $t_R$=9.95 min, analytical HPLC conditions: column=YMC ODS-A S-3 120 Å, mobile phase/gradient: 95% water (+0.025% formic acid)/acetonitrile (+0.025% formic acid) to 5% water in 6 minutes, hold at 5% for 9 minutes, flow=0.30 mL/min) The MS data is provided in Table 7:

| Exact Mass High Resolution Results | | | | | |
|---|---|---|---|---|---|
| Adduct | Exptl. | Exact | mmu | ppm | RI % |
| [M + H]1+ | 1025.62887 | 1025.63084 | −1.97 | −1.92 | 38.0 |

Example 8

Mesencephalic dopaminergic neuron cultures were prepared as described in Pong et al., J. Neurochem. 69: 986-994, 1997, which is incorporated herein by reference in its entirety. Embryonic day 15 (E15) rat fetuses were collected and dissected in ice-cold phosphate-buffered saline (PBS). The ventral piece of tissue compromising the mesencephalic dopaminergic region was dissected out. Dissected pieces of tissue were pooled together and transferred to an enzymatic dissociation medium containing 20 IU/mL papain in Earle's balanced salt solution (Worthington Biochemical, Freehold, N.J., USA) and incubated for 60 minutes at 37° C. After enzymatic dissociation, the papain solution was aspirated and the tissue mechanically triturated with a fire-polished glass Pasteur pipette in complete medium (equal volumes of minimum essential medium (MEM) and F-12 nutrient mixture (GibcoBRL) supplemented with 0.1 mg/mL apotransferrin and 2.5 μg/mL insulin) containing 2,000 IU/mL DNase and 10 mg/mL ovomucoid protease inhibitor.

For dopamine uptake experiments, single-cell suspensions in complete media were seeded on poly-L-ornithine and laminin coated 24-well plates. The cultures were maintained for seven days prior to experimentation. Cultures were pretreated with various concentrations of the compound for 24 hours, then exposed to 10 mM MPP+ for 1 hour. Following the 1 hour incubation, media was exchanged three times and fresh compound was added for an additional 48 hours.

After 48 hours growth of mesencephalic dopaminergic neuron cultures following MPP+ exposure, high-affinity 3H-dopamine uptake was performed using a modified method described by Prochiantz et al., Nature 293: 570-572, 1981, which is incorporated herein by reference. Cultures were washed with pre-warmed PBS containing 5.6 mM glucose and 1 mM ascorbic acid. Cultures were then incubated for 15 minutes at 37° C. with 50 nM 3H-dopamine (31 Ci/mmol, DuPont-NEN, Wilmington, Del., USA). The cultures were washed twice with buffer and lysed with 0.5 N NaOH. The lysate was transferred to a scintillation vial containing Ultima Gold scintillation cocktail and radioactivity was determined with a liquid scintillation counter. Alternatively, culture lysates can be washed twice with buffer, incubated for 2 hours at room temperature with Optiphase Supermix scintillation cocktail (Wallac Scintillation Products, Gaithersburg, Md., USA), and radioactivity measured with a liquid scintillation counter.

Dissociated cortical neuron cultures were prepared as previously described (Pong et al., 2001). Briefly, embryonic day 15 rat fetuses were collected and dissected in ice-cold PBS. Dissected cortices were pooled together and transferred to an enzymatic dissociation medium containing papain. After 30 minutes, the tissue was mechanically triturated with a fire-polished glass Pasteur pipette. Single-cell suspensions in complete media were seeded on poly-L-ornithine and laminin coated 96-well plates. After 24 hours, cultures were treated with various concentrations of compound for 72 hours. The cultures were then fixed and stained with an anti-tubulin primary antibody (TUJ-1) and a fluorescent-tagged secondary antibody. Neurite outgrowth was determined by using the Enhanced Neurite Outgrowth (ENO) algorithm with the Cellomics ArrayScan and expressed as average neurite length or total neurite length per cell.

Spinal cord neuron cultures were prepared from embryonic day 15 (E15) rat embryos (Sprague-Dawley, Charles River Laboratories, Wilmington, Mass.). The embryos were collected and their spinal cords were removed in ice-cold phosphate-buffered saline (PBS) without $Ca^{2+}$ and $Mg^{2+}$. Dissected pieces of spinal cord tissue were pooled together and transferred to an enzymatic dissociation media containing 20 IU/mL papain in Earle's balanced salt solution (Worthington Biochemical, Freehold, N.J.) and incubated for 30 minutes at 37° C. After enzymatic dissociation, the papain solution was aspirated and the tissue mechanically triturated with a fire-polished Pasteur pipette in complete media [Neurobasal Medium with B-27 supplement (Gibco, Grand Island, N.Y.), 100 IU/mL penicillin, 100 μg/mL streptomycin, 3.3 μg/mL aphidicolin, 0.5 mM glutamate] containing 2,000 IU/mL DNase and 10-mg/mL ovomucoid protease inhibitor. Single-cell suspensions in complete media were plated on pre-coated poly-L-ornithine/laminin 96-well plates (Becton-Dickinson, Bedford, Mass.) at a density of $1.0 \times 10^4$ cells/well. Spinal cord neurons were maintained for 24 h then exposed to vehicle or various concentrations of compound for 72 h.

The compounds of Examples 1-3 were all active in cortical neuron assays with an $EC_{50}$ less than 1 µM. The compounds of Examples 1 and 6 were all active in dopaminergic uptake assays with an $EC_{50}$ less than 1 µM. The compounds of Examples 1-3 and 6 were all active in spinal cord neuron assays with an $EC_{50}$ less than 1 µM In comparison, CCI-779 and rapamycin were considered inactive in cortical neuron assays and dopaminergic uptake assays with $EC_{50}$ values of greater than 1 µM. Rapamycin phenyltriazolinedione was active in the dopaminergic uptake assay with an $EC_{50}$ value of less than 1 µM.

Example 9

Permanent Occlusion of Middle Cerebral Artery (pMCAO)

Adult male Wistar rats (Charles River, Wilmington, Mass.) 270-300 g were anesthetized with 3% isoflurane in 70% nitrous oxide and 30% oxygen through a nose cone. Temperature was maintained at 37° C. throughout the surgery using a heating lamp. Permanent occlusion of MCAO was induced by electro cauterization of the distal portion of the MCA (via a craniotomy) with a 90 min ligation of both carotid arteries to interrupt collateral circulation (Chen S T, Hsu C Y, Hogan E L, Maricq H Balentine J D (1986) A model of focal ischemic stroke in the rat: reproducible extensive cortical infarction. Stroke 17:738-743). Compound was administered 10 mg/kg i.v. 1.5, 5.5, 24, 48, and 72 hours post ischemia. Rats were kept for 21 day for long-term functional recovery evaluation. Three behavioral tests, modified from earlier tests reported by Bederson et al., (Bederson J B, Pitts L H, Tsuji M, Nishimura M C, Davis R L, Bartkowski H (1986) Rat middle cerebral artery occlusion: evaluation of the model and development of a neurologic examination. Stroke 17(3): 472-476) and DeRyck et al. (DeRyck M, van Reempts J, Duytschaever H, van Deuren B, Clincke G (1992) Neocortical localization of tactile/proprioceptive limb placing reactions in the rat. Brain Res 573:44-60), were used to assess sensorimotor and reflex function. Briefly, for the postural test, rats were suspended from the tail approximately 30 cm above the bench top. Rats extending both forelimbs toward the table were scored as 0, flexing contralateral limb toward the body and/or rotating the contralateral shoulder and limb medially were scored as 1, and rolling up the body toward the contralateral side and attempting to grasp the tail were scored as 2. The forelimb placement test is comprised of two subtests, visual and tactile placing test. For visual placing test, rats were held with forelimbs hanging free and were brought close either from front or sideway to a tabletop. For tactile placing test, the rats were held so that it cannot see the tabletop. The dorsal and lateral surface of the forepaw touched lightly to the tabletop. For each test, scoring was, 0 if the placing response was immediate and normal; 1 if the placing was delayed (>2 seconds) or occasional; 2 if there was no response. For hind limb placement test, rats were held on the edge of the bench top and the contralateral hind limb was pulled off the edge and released. Rats retracting hind limb back on bench top immediately were scored as 0, delaying (>2 seconds) were scored as 1, and unable to retract hind limb were score as 2. Total Score was ranged from 0 to 12. The compound prepared in Example 2 showed statistically significant reduction of behavior deficit scoring in rats after I.V. administration (10 mg/kg) following pMCAO.

Example 10

T-Cell Assays

In the following assays, human CD4+ T cells were purified by negative selection from peripheral blood lymphocytes using RosetteSep as per manufacture's instructions (StemCell Technologies, Inc. Vancouver, British Columbia).

A. Anti-CD3/-CD28 Stimulation and IL-2 Re-stimulation Assay

Tosyl-activated magnetic microspheres (Dynal, Great Neck, N.Y.) were coated with anti-CD3 Ab (1 µg/$10^7$ microspheres), and anti-CD28Ab (0.5 µg/$10^7$ microspheres) as described in Blair et al. J. Immunol., 160:12, 1998. Murine IgG was used to saturate the binding capacity of the microspheres (total protein=5 µg/$10^7$ microspheres). Protein-coated microspheres were added to purified CD4+ T cells ($2\times10^6$ cells/mL, ratio 1 bead:1 cell) and activated for 72 hours in RPMI, 10% fetal calf serum, 2 mM glutamine media. Cells were harvested, washed, and cultured overnight in fresh media and re-stimulated with IL-2 as described in Bennett et al., J. Immunol. 170:711, 2003. Briefly, overnight rested cells were recounted, plated ($10^5$ cells/well) in flat-bottomed 96 well microtiter plates and stimulated with 1 ng/mL human IL-2 (R&D Systems, Minneapolis, Minn.) in the presence of increasing concentrations of compound. Seventy-two hours after culture re-stimulation, plates were pulsed with 1 µCi/well tritiated thymidine and incubated for a 6-16 hour period.

The compounds of Examples 1 and 3 inhibited IL-2 production with $IC_{50}$ less than about 1 µM, and preferably less than about 200 nM. The IL-2 production of the compounds of Examples 1 and 3 were commensurate with the IL-2 production of rapamycin and CCI-779.

B. Phorbol 12-myristate 13-acetate (PMA)/Ionomycin Activation Assay

Proliferation of the compounds was determined using this assay. CD4+ T cells ($5\times10^5$ cells/well) were plated in flat bottomed 96 well microtiter plates in RPMI, 10% fetal calf serum, 2 mM glutamine media and stimulated with PMA (10 ng/mL) and ionomycin (200 ng/mL) in the presence of increasing concentration of compound. Seventy-two hours after activation, 100 µL of culture media was collected for IL-2 determination, an additional 100 µL fresh media was added to each well and cultures labeled with tritiated thymidine (1 µCi/well) for 6 hours. Cultures were harvested and tritiated thymidine incorporation (count per minute, CPM) assessed using a Trilux (Perkin Elmer, Shelton, Conn.). IL-2 production was determined using an ELISA as per manufacture's instructions (R&D Systems, Minneapolis, Minn.).

In this assay, the compounds of Examples 1 and 3 inhibited proliferation with $EC_{50}$ ranging 4.9-0.2 µM.

Example 11

The PTEN-tumor suppressor gene (phosphate and tensin homolog deleted on chromosome ten) encodes a lipid phosphatase that plays a critical role in the negative regulation of PI3K/AKT signaling pathways. Mutation or deletion of the PTEN gene has been found in tumors of brain, prostate, endometrium, thyroid, breast and lymphoid tumors. See, Cantley et al., Proc. Natl. Acad. Sci. USA. 96: 4240-4245, 1999; Ali et al., J. Natl Cancer Inst. 91: 1922-32, 1999; Scott et al., Proc. Natl. Acad. Sci. USA. 95: 7772-7777, 1998; and Nave et al., Biochem. J. 344: 427-431, 1999.

In this assay, a cell-based proliferation assay was performed to evaluate the compounds of the invention in inhibiting growth of cells including the breast tumor cell line MDA468 (PTEN-mutated) ATCC No. HTB-132 or prostate tumor cell line LNCap (PTEN-mutated) ATCC CRL-1740.
  (i) On day one, cells were plated in 96-well culture plates.
  (ii) On day two, compounds were added to cells at a predetermined concentration.
  (iii) On day five, cell proliferation was measured by standard MTS assay protocol as described in SA O'Toole et al., Cancer Detection and Prevention, 27(1), 2003. Results were recorded by A490 absorbance using a 96-well format platereader.
  (iv) The MTS results (A490 units) from compound-treated wells were then calculated as % control growth relative to the control (untreated) wells on the same culture plate.

This data illustrates that the compound of Example 1 had $IC_{50}$ values of less than 0.010M for both MDA468 and LNCap cell lines.

Example 12

Modulation of Ryanodine Receptor Calcium Currents

Compounds are expected to modulate ryanodine receptor calcium currents via stabilization of FKBP12.6 binding to the ryanodine receptor when tested in the following assays:

A. Calcium Uptake Assay

Calcium ($Ca^{2+}$) uptake is determined by the procedures described in (1) T. Yamamoto, et al., Cardiovascular Research, 44:146-155 (1999) or (2) M. Yano, et al., Circulation, 102:2131-2136 (2000).

Sarcoplasmic reticulum (SR) vesicles for use in these assays are prepared according to the method of Kranias, et al., Biochem. Biophys. Acta., 709:28-37 (1982). Left ventricles obtained from dogs with induced heart failure are homogenized in a solution containing 30 mM Tris-malate, 0.3 M sucrose, 5 mg/L leupeptin and 0.1 mM PMSF, at pH 7.0 (Solution I). The homogenate is centrifuged at 5500 g for 10 minutes and the resultant supernatant filtered through four layers of cheesecloth before centrifugation at 12,000 g for 20 minutes. The supernatant is again filtered through cheesecloth and centrifuged at 143,000 g for 30 minutes. The pellet is re-suspended in a solution containing 0.6 M KCl, 30 mM Tris-malate, 0.3 M sucrose, 5 mg/L leupeptin, 0.1 mM PMSF, at pH 7.0 (Solution 11). The suspension is centrifuged at 143,000 g as described above. The pellet is suspended in Solution I and centrifuged at 143,000 g. The pelleted microsomal fraction containing SR vesicles is suspended in a solution containing 0.1 M KCl, 20 mM Tris-malate, 0.3 M sucrose, 5 mg/L leupeptin, 0.1 mM PMSF, at pH 7.0, to give a final protein concentration of 10-20 mg/mL.

(1) SR vesicles as prepared above (0.2 mg/mL) are incubated in 2 mL of a solution containing 0.15 M KCl, 1 mM $MgCl_2$, 30 µM $^{45}CaCl_2$ (1 mCi/mL), 10 mM $NaN_3$ and 20 mM MOPS, pH 7.1 (22° C.). $Ca^{2+}$ uptake is initiated by addition of 1 mM ATP and is determined at varying time intervals by placing a 2 mL aliquot on a 0.45 µm Millipore filter, and rinsing it with 5 mL of washing buffer (0.15 MKCl, 20 mM MOPS, pH 7.1 (22° C.), containing 30 mM EGTA and 15 µM ruthenium red).

Radioactivity retained on the filters is determined by liquid scintillation counting.

(2) SR vesicles as prepared above (0.2 mg/mL) are incubated in 0.5 mL of a solution containing 0.15 mol/L potassium gluconate, 1 mmol/L $MgCl_2$, 0.2 mmol/L EGTA-calcium buffer (free [$Ca^{2+}$] 0.3 µM), 10 mM $NaN_3$, and 20 mM MOPS, pH 6.8. $Ca^{2+}$ uptake is initiated by the addition of 0.5 mM ATP into the cuvette. $Ca^{2+}$ uptake is monitored over time spectrophotometrically with fluo 3 as a $Ca^{2+}$ indicator (excitation at 480 nm, emission at 530 nm).

B. Calcium Leak Assay

Calcium ($Ca^{2+}$) uptake is determined by the procedures described in M. Yano, et al., Circulation, 102:2131-2136 (2000).

Following a plateau in $Ca^{2+}$ uptake in SR vesicles according to the procedure described in "A. Calcium Uptake Assay, (2)" above, varying concentrations of FK506 are added in the presence of 1 µM thapsigargin to inhibit SR $Ca^{2+}$-ATP activity, and the resultant $Ca^{2+}$ leak is monitored.

C. Co-Localization Assay

Co-localization of cardiac ryanodine receptor (RyR) to FKBP12 (or FKBP12.6) is determined by the procedures described in C. George, et al., Circulation Research, 93:531-540 (2003).

HL-1 cardiomyocytes expressing the human cardiac ryanodine 2 receptors ($hRyR_2$) are cultured on a gelatin (0.02% [wt/vol]/fibronectin (10 µg·mL) matrix and are maintained in Claycomb media (JRH Biosciences) supplemented with fetal calf serum (10% [vol/vol], glutamine (2 mM), norepinephrine (0.1 mM), penicillin (100 u/mL), and streptomycin (100 µg/mL). FKBP12.6: $hRyR_2$ interaction is determined using coimmunoprecipitation assays using pAb129 (anti-$RyR_2$) and anti-FKBP to immunoprecipitate and immunoblot, respectively.

RyR2 is immunolocalized using pAb129 and $Alexa^{488}$ conjugated secondary antibodies and FKBP is co-stained using N-19 (Santa Cruz Biotechnology) and $Alexa^{546}$ secondary antibodies.

D. Western Blots

Expression and association between cardiac ryanodine receptor (RyR) to FKBP12 (or FKBP12.6) is determined by the procedures described in C. George, et al., Circulation Research, 93:531-540 (2003).

Western blots of microsomal fractions obtained from HL-1 cardiomyocytes cultured as described above in "C. Co-Localization Assay" may be carried out using conventional techniques. Microsomal fractions (100 µg) from HL-1 cells are immunoprecipitated using anti-$RyR_2$ (pAb129) followed by anti-FKBP immunoblotting.

E. Electrophysiological Determination of SR $Ca^{2+}$ Leak

Sarcoplasmic reticulum (SR) $Ca^{2+}$ leak is determined by the procedures described in T. Shannon, et. al., Circ. Res., 93: 592-594 (2003).

Ventricular myocytes are isolated from New Zealand White rabbits (Myrtle's Rabbitry, Inc., Thompson Station, Tenn., USA) in which heart failure is induced by combined aortic insufficiency and stenosis. Diastolic SR $Ca^{2+}$ is measured during cellular stimulation to steady state at different frequencies to vary load. Levels of diastolic ryanodine receptor (RyR) $Ca^{2+}$ leak may be assessed by the increased total sarcoplasmic reticulum $Ca^{2+}$ load ([$Ca^{2+}$]$_{SRT}$) upon inclusion of tetracaine (an RyR blocker).

Example 13

Cardiovascular Effect

The ability of the compounds of this invention to treat or inhibit cardiovascular disease or peripheral vascular disease is confirmed in a standard pharmacological test procedure using ApoE knockout (EKO) mice, which is a well accepted animal model of human atherosclerosis. The procedure used is briefly summarized below.

Male EKO mice, 4-6 weeks of age, are housed in shoe-box cages and are allowed ad lib. food and water. The animals are randomized by weight into 5 groups (N=12-15 mice per group) and are fed Purina Rodent Chow for the first week of the study. Also during this period as well as the remaining 12 weeks of the study, the animals are dosed every 2 days with 0, 1, 2, 4 or 8 mg/kg rapamycin analogue subcutaneously (s.c.) using 2% Tween-80, 1% carboxymethyl cellulose as the vehicle and Control. The animal diet is switched to a casein-based Western Diet for week 2 to week 13 of the study. At the end of the study period, the animals are euthanized, plasma samples obtained, and the hearts perfused first with saline, then with 10% formalin. Total cholesterol and triglycerides are determined using enzymatic methods with commercially-available kits from Boehringer Mannheim and Wako Biochemicals, respectively, and the Boehringer Mannheim Hitachii 911 Analyzer (Boehringer Mannheim Diagnostic Laboratory Systems, Indianapolis, Ind.). Separation and quantification of plasma lipoproteins are performed using FPLC size fractionation. Briefly, 50-100 ml of serum is filtered and injected into two Superose 6 columns (Amersham Pharmacia Biotech, UK, Ltd) connected in series and eluted at a constant flow rate with 1 mM sodium EDTA and 0.15 M NaCl. Areas of each curve representing VLDL, LDL and HDL are integrated using Millennium software (Waters Technologies Corporation), and each lipoprotein fraction was quantified by multiplying the Total Cholesterol value by the relative percent area of each respective peak. The aortas are carefully isolated and remain in the formalin fixative for 48-72 hours before handling. Atherosclerotic lesions are identified by Oil Red 0 staining, a well accepted procedure for identifying accumulation of neutral lipids such as cholesterols and triglycerides. The vessels are destained, and then imaged using a Nikon SMU800 microscope fitted with a Sony 3CCD video camera system in concert with IMAQ Configuration Utility (National Instrument) as the image capturing software. The lesions are quantified along the aortic arch using a custom threshold utility software package designed by Robert Coll (Coleman Technologies). Automated lesion assessment is performed on the vessels using the threshold function of the program, specifically on the region contained within the aortic arch from the proximal edge of the Right Common Carotid artery to the distal edge of the Left Subclavian artery. Aortic atherosclerosis data is expressed as percent lesion (lipid) involvement strictly within this defined luminal area. Statistical significance between the Control and treated groups is determined using the Dunnett's Test at 1% significance level ($p<0.01$).

The results are anticipated to show that treatment with a compound of the invention significantly ($p<0.01$) increases levels of circulating plasma HDL-cholesterol and LDL-cholesterol, while not significantly affecting levels of triglycerides, total cholesterol, or VLDL-cholesterol compared with control EKO mice. It is also anticipated that the results will show a marked and dramatic decrease in the level of atherosclerosis (lipid deposition) in the treated mice.

The results are also expected to show that the compound of the invention protect against fat accumulation in the vascular wall, and the development of the classically described, atherosclerotic disease.

All patents, patent publications, and other publications listed in this specification are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. A pharmaceutical composition comprising a pharmaceutically acceptable excipient or carrier and a compound of the formula I:

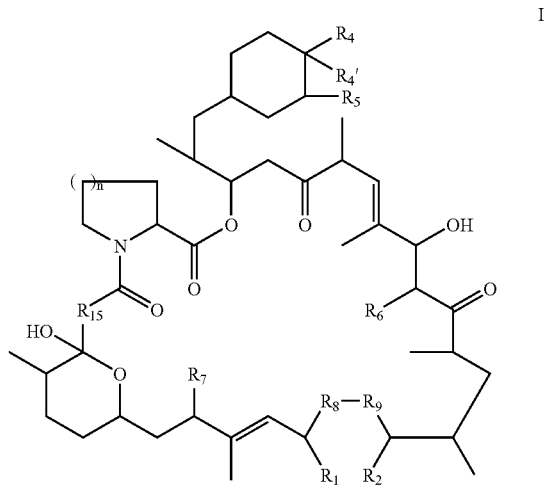

wherein:
$R_1$ and $R_2$ are different, independent groups and are selected from the group consisting of $OR_3$ and $N(R_{3'})(R_{3''})$; or
$R_1$ and $R_2$ are different, are connected through a single bond, and are selected from the group consisting of O and $NR_3$;
$R_3$, $R_{3'}$, and $R_{3''}$ are independently selected from the group consisting of H, $C_1$ to $C_6$ alkyl, $C_1$ to $C_6$ substituted alkyl, $C_3$ to $C_8$ cycloalkyl, substituted $C_3$ to $C_8$ cycloalkyl, aryl, substituted aryl, heteroaryl, and substituted heteroaryl;
$R_4$ and $R_{4'}$ are:
  (a) independently selected from the group consisting of H, OH, O($C_1$ to $C_6$ alkyl), O(substituted $C_1$ to $C_6$ alkyl), O(acyl), O(aryl), O(substituted aryl), and halogen; or
  (b) taken together to form a double bond to O;
$R_5$, $R_6$, and $R_7$ are independently selected from the group consisting of H, OH, and $OCH_3$;
$R_8$ and $R_9$ are connected through a single bond and are $CH_2$;
$R_{15}$ is selected from the group consisting of C=O, CHOH, and $CH_2$;
n is 1 or 2;
wherein the acyl group is HC(O)- or a —C(O)R'''-group, wherein R''' is selected from $C_1$ to $C_6$ alkyl, substituted alkyl, and alkoxy;
wherein the heteroaryl group is a monocyclic, aromatic 4- to 7-membered ring having one to four heteroatoms independently selected from N, S and O;

wherein the aryl group is an aromatic system of 6-20 carbon atoms in a single or multiple ring fused or linked ring system wherein at least one part of the fused or linked rings forms the conjugated system;

wherein the substituents for the substituted alkyl, aryl, heteroaryl, or acyl are one or more substituents independently selected from halogen, CN, OH, $NO_2$, amino, aryl, a heterocyclic ring consisting of a monocyclic, saturated, partially unsaturated, or wholly unsaturated 4- to 7-membered ring having 1 to 4 heteroatoms independently selected from N, S, O, alkoxy, aryloxy, alkylcarbonyl, alkylcarboxy, and arylthio;

or a pharmaceutically acceptable salt thereof.

2. The composition according to claim 1, wherein said $R_1$ and $R_2$ are connected through a single bond.

3. The composition according to claim 1, wherein $R_1$ is O, $R_2$ is $NR_3$.

4. The composition according to claim 1, wherein $R_1$ is $OR_3$ and $R_2$ is $N(R_{3'})(NR_{3''})$.

5. The composition according to claim 1, wherein $R_3$, $R_{3'}$ or $R_{3''}$ is an aryl or substituted aryl.

6. The composition according to claim 5, wherein said substituted aryl is a substituted benzene ring.

7. The composition according to claim 6, wherein said aryl or substituted aryl is of the structure:

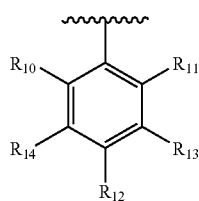

wherein:
$R_{10}$, $R_{11}$, $R_{12}$, $R_{13}$, and $R_{14}$ are independently selected from the group consisting of H, $C_1$ to $C_6$ alkyl, substituted $C_1$ to $C_6$ alkyl, aryl, substituted aryl, heteroaryl, substituted heteroaryl, halogen, acyl, OH, O(alkyl), O(substituted alkyl), O(aryl), O(substituted aryl), O(acyl), $NH_2$, NH(alkyl), NH(substituted alkyl), NH(aryl), N H(substituted aryl), and NH(acyl).

8. The composition according to claim 1, wherein $R_4$ or $R_{4'}$ is OH.

9. The composition according to claim 1, wherein $R_4$ or $R_{4'}$ is O(acyl).

10. The composition according to claim 1, wherein $R_5$, $R_6$, and $R_7$ are $OCH_3$.

11. The composition according to claim 10, wherein said acyl is:

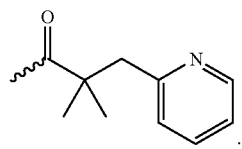

12. The composition according to claim 1, wherein n is 2.

13. The composition according to claim 1, wherein $R_{15}$ is C=O.

14. The composition according to claim 1, selected from the group selected from the group consisting of 9,27-dihydroxy-3-{2-[4-hydroxy-3-methoxycyclohexyl]-1-methylethyl}-10,21-dimethoxy-6,8,12,14,20,26-hexamethyl-37-phenyl-4,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentriacontine-1,5,11,28,29(6H,31H)-pentone;

9,27-dihydroxy-3-{2-[4-hydroxy-3-methoxycyclohexyl]-1-methylethyl}-10,21-dimethoxy-6,8,12,14,20,26-hexamethyl-37-phenyl-4,9,10,12,13,14,15,16,17,18,21,22,23,24,25,26,27,32,33,34,34a-henicosahydro-3H-23,27-epoxy-18,15-(epoxyimino)pyrido[2,1-c][1,4]oxazacyclohentriacontine-1,5,11,28,29(6H,31H)-pentone;

37-(4-chloro-3-methylphenyl)-9,27-dihydroxy-3-{-2-[4-hydroxy-3-methoxycyclohexyl]-1-methylethyl}-10,21-dimethoxy-6,8,12,14,20,26-hexamethyl-4,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentr;acontine-1,5,11,28,29(6H,31H)-pentone;

37-(2,6-dichlorophenyl)-9,27-dihydroxy-3-{2-[4-hydroxy-3-methoxycyclohexyl]-1-methylethyl}-10,21-dimethoxy-6,8,12,14,20,26-hexamethyl-4,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentriacontine-1,5,11,28,29(6H,31H)-pentone;

9,27-dihydroxy-3-{-2-[4-hydroxy-3-methoxycyclohexyl]-1-methylethyl}10,21-dimethoxy-6,8,12,14,20,26-hexamethyl-37-phenyl-4,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentriacontine-1,5,11,28,29(6H,31H)-pentone ester with -2,2-dimethyl-3-(pyridin-2-yl)-propionic acid; and 37-(2,6-dichlorophenyl)-9,27-dihydroxy-3-{-2-[4-hydroxy-3-methoxycyclohexyl]-1-methylethyl}-10,21-dimethoxy-6,8,12,14,20,26-hexamethyl-4,9,10,12,13,14,15,18,21,22,23,24,25,26,27,32,33,34,34a-nonadecahydro-3H-23,27-epoxy-18,15-(epoxyimino)pyrido[2,1-c][1,4]oxazacyclohentriacontine-1,5,11,28,29(6H,31H)-pentone; or pharmaceutically acceptable salts of each of these.

15. The composition according to claim 1, wherein $R_1$ is $OR_3$; $R_2$ is $N(R_{3'})(R_{3''})$; $R_3$ is H; $R_{3'}$ is H; $R_{3''}$ is phenyl; $R_4$ is OH; $R_5$-$R_7$ are $OCH_3$.

16. The composition according to claim 1, wherein $R_1$ and $R_2$ are connected through a single bond; $R_1$ is O; $R_2$ is $NR_3$; $R_3$ is phenyl; $R_4$ is OH; $R_5$-$R_7$ are $OCH_3$.

17. The composition according to claim 1, wherein $R_1$ and $R_2$ are connected through a single bond; $R_1$ is O; $R_2$ is $NR_3$; $R_4$ is OH; $R_5$-$R_7$ are $OCH_3$; and $R_3$ is

18. The composition according to claim 1, wherein $R_1$ and $R_2$ are connected through a single bond; $R_1$ is O; $R_2$ is $NR_3$; $R_4$ is OH; $R_5$-$R_7$ are $OCH_3$; and $R_3$ is
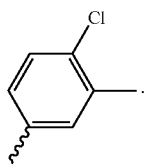
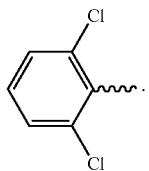
19. The composition according to claim 1, wherein $R_1$ and $R_2$ are connected through a single bond; $R_1$ is O; $R_2$ is $NR_3$; $R_3$ is phenyl; R5-R7 are $OCH_3$; and $R_4$ is
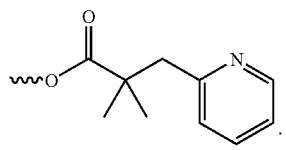
20. The composition according to claim 1, wherein the compound is
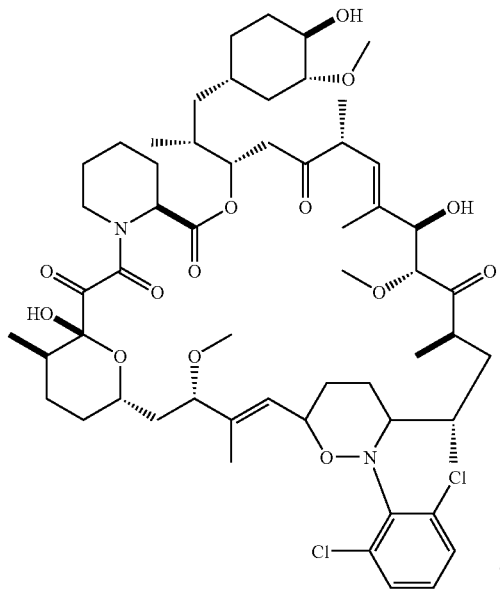
* * * * *

UNITED STATES PATENT AND TRADEMARK OFFICE
CERTIFICATE OF CORRECTION

PATENT NO.        : 7,470,682 B2
APPLICATION NO.   : 11/893090
DATED             : December 30, 2008
INVENTOR(S)       : Graziani et al.

Page 1 of 1

It is certified that error appears in the above-identified patent and that said Letters Patent is hereby corrected as shown below:

In column 34, line 45, Claim 1,
    Change "$R_3$, $R_3$, and $R_3$" to -- $R_3$, $R_{3'}$, and $R_{3''}$ --.

In column 36, line 24, Claim 14,
    Change "oxazacyclohentr;acontine" to -- oxazacyclohentriacontine --.

In column 37, line 22, Claim 19,
    Change "R5-R7" to -- $R_5$-$R_7$ --.

Signed and Sealed this

Seventh Day of April, 2009

JOHN DOLL
*Acting Director of the United States Patent and Trademark Office*